United States Patent
Oh et al.

(10) Patent No.: US 11,726,082 B2
(45) Date of Patent: Aug. 15, 2023

(54) SCREENING METHOD OF DRUG CANDIDATES FOR TREATING DISEASE USING INTERACTION BETWEEN CALCIUM AND PHOSPHATIDYLINOSITOL PHOSPHATE

(71) Applicants: Gachon University of Industry—Academic Cooperation Foundation, Seongnam-si (KR); Gil Medical Center, Incheon (KR)

(72) Inventors: Byung-Chul Oh, Incheon (KR); Jin Ku Kang, Incheon (KR); Ok Hee Kim, Incheon (KR); Cheol Soon Lee, Incheon (KR)

(73) Assignees: GACHON UNIVERSITY OF INDUSTRY-ACADEMIC COOPERATION FOUNDATION, Gyeonggi-Do (KR); GIL MEDICAL CENTER, Incheon (KR)

(*) Notice: Subject to any disclaimer, the term of this patent is extended or adjusted under 35 U.S.C. 154(b) by 1284 days.

(21) Appl. No.: 16/198,188

(22) Filed: Nov. 21, 2018

(65) Prior Publication Data
US 2019/0154666 A1   May 23, 2019

(30) Foreign Application Priority Data
Nov. 22, 2017  (KR) .................. 10-2017-0156849

(51) Int. Cl.
G01N 33/50   (2006.01)
A61K 38/28   (2006.01)

(52) U.S. Cl.
CPC ......... *G01N 33/5035* (2013.01); *A61K 38/28* (2013.01); *G01N 33/5011* (2013.01); *G01N 2500/02* (2013.01)

(58) Field of Classification Search
CPC ............................................... G01N 2500/00
See application file for complete search history.

(56) References Cited

U.S. PATENT DOCUMENTS

2017/0199174 A1* 7/2017 Oh .................... G01N 33/5011

FOREIGN PATENT DOCUMENTS

KR   1020140039322 A   4/2014
KR   1020160139072 A   12/2016

OTHER PUBLICATIONS

Schmitz-Peiffer et al., "Protein kinase C function in muscle, liver, and beta-cells and its therapeutic implications for type 2 diabetes," Diabetes 2008;57(7):1774-83. PMID: 18586909. (Year: 2008).*
Cullen M. Taniguchi, Brice Emanuelli, and C. Ronald Kahn, Critical Nodes in Signalling Pathways: Insights into Insulin Action, National Reviews, Molecular Cell Biology, Feb. 2006, pp. 85-96, vol. 7.
Steven E. Kahn, Rebecca L. Hull, and Kristina M. Utzschneider, Mechanisms Linking Obesity to Insulin Resistance and Type 2 Diabetes, Insight Review, Nature, Dec. 14, 2006, pp. 840-846, vol. 444, doi: 10.1038/nature05482.
Varman T. Samuel and Gerald I. Shulman, Integrating Mechanisms for Insulin Resistance: Common Threads and Missing Links, NIH-PA Author Manuscript, Cell, Mar. 2, 2012, pp. 852-871, vol. 148(5).
Byung-Chul Oh, Myung Hee Kim, Bong-Sik Yun, Won-Chan Choi, Sung-Chun Park, Suk-Chul Bae, and Tae-Kwang Oh, Ca2+-Inositol Phosphate Chelation Mediates the Substrate Specificity of Beta-Propeller Phytase, Biochemistry, 2006, pp. 9531-9539, vol. 45.

* cited by examiner

*Primary Examiner* — Theodore R. Howell
(74) *Attorney, Agent, or Firm* — Workman Nydegger

(57) ABSTRACT

The present invention relates to a method for screening drug candidates for treating a disease using the interaction between calcium and phosphatidylinositol phosphate. Particularly in the present invention, it was confirmed that the concentration of calcium was increased in the obesity induced insulin resistance animal model and the increased calcium concentration inhibited the migration of Akt protein containing PH domain and the signal transduction, while the protein containing C2 domain was able to migrate to the cell membrane by binding to calcium/PIP complex even under the condition of high calcium concentration. Therefore, the investigation of the interaction between calcium and PIP can be a useful method for screening of drug candidates for treating metabolic disease, cancer or hypertension.

12 Claims, 24 Drawing Sheets
(19 of 24 Drawing Sheet(s) Filed in Color)
Specification includes a Sequence Listing.

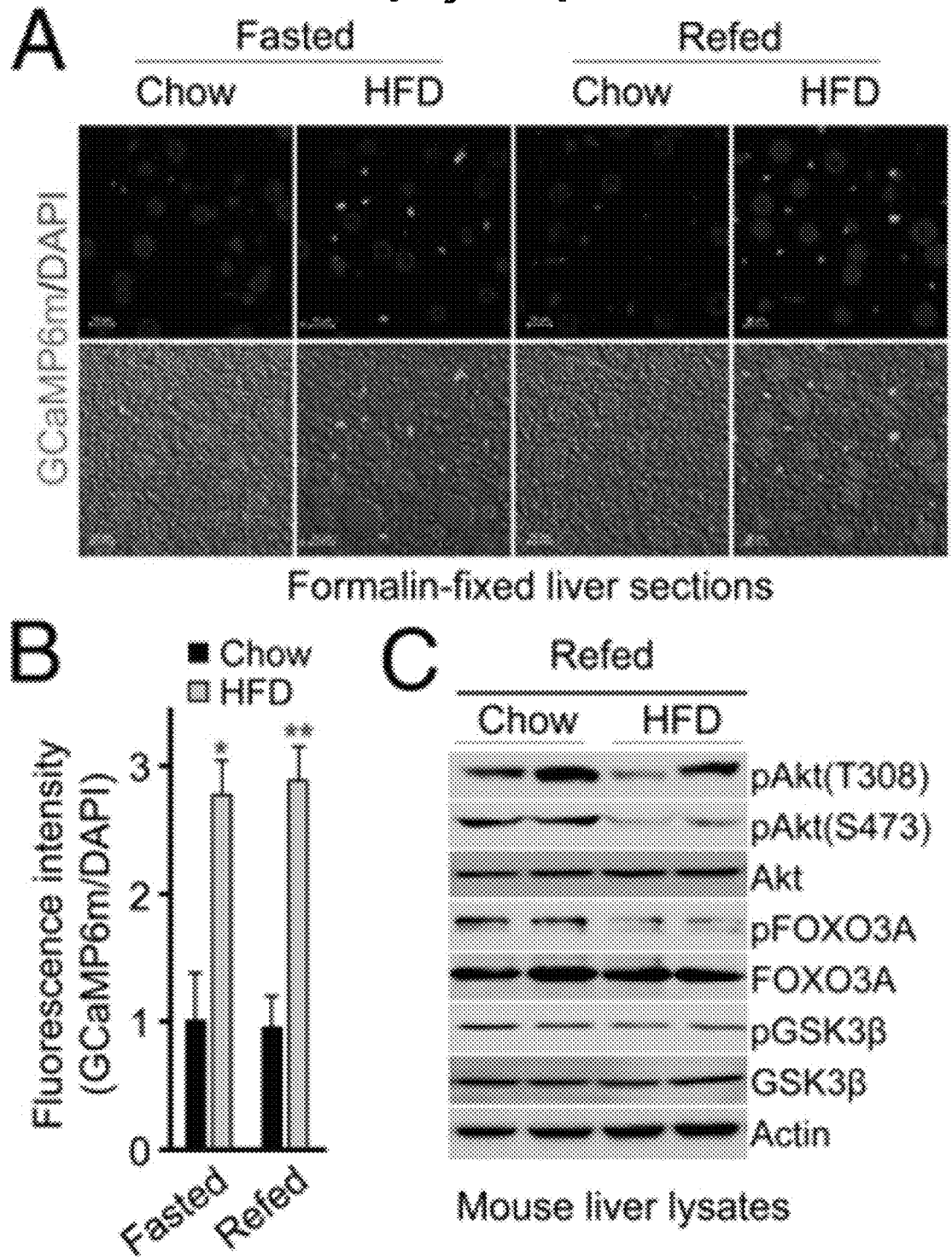

[Figure 2]
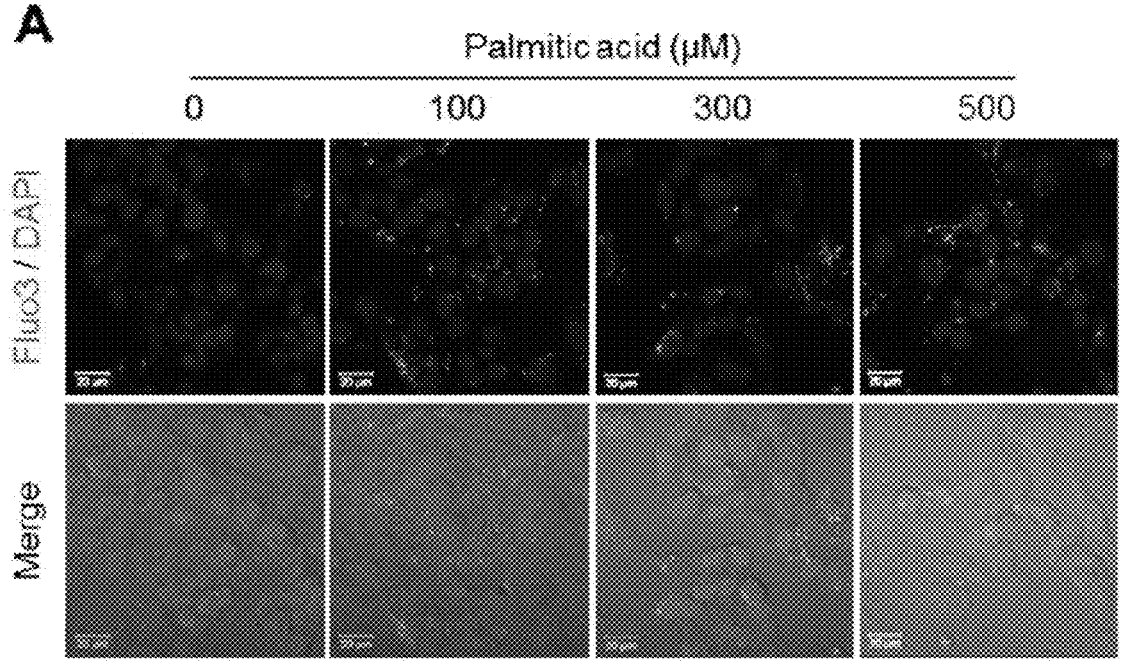
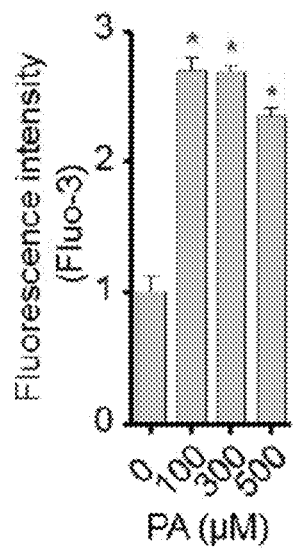
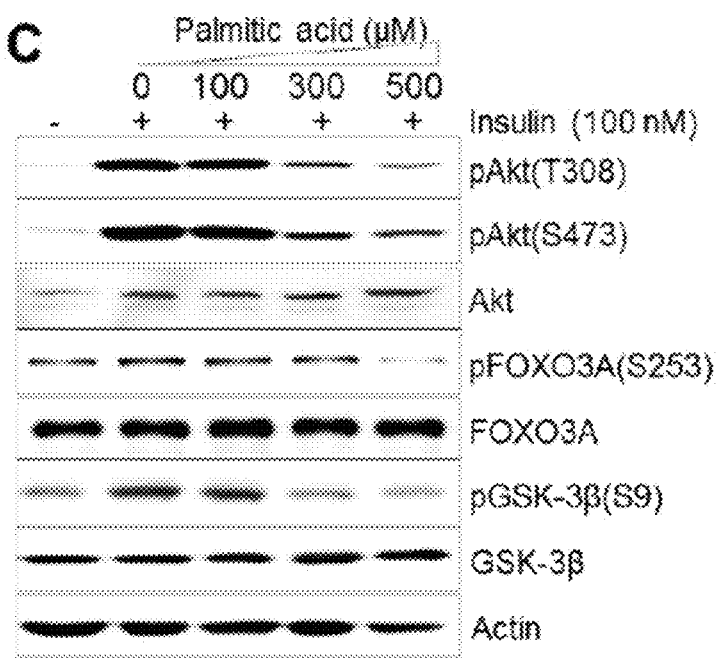

[Figure 3]
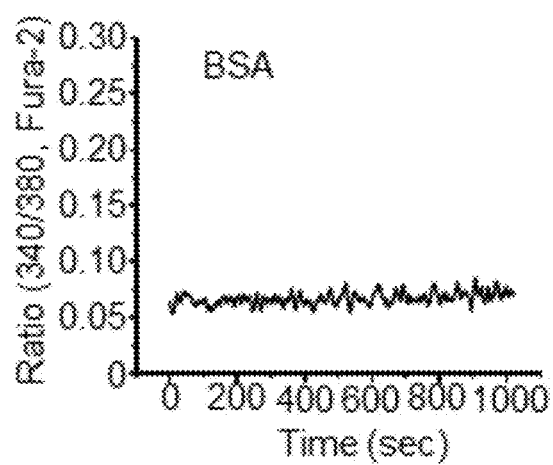
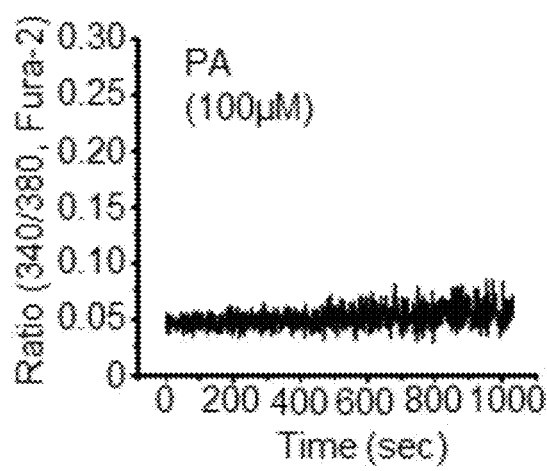
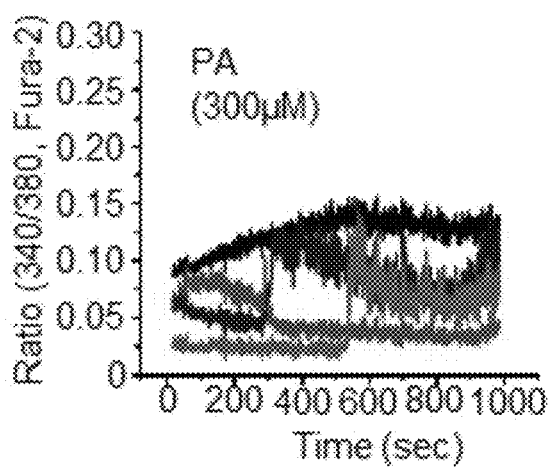
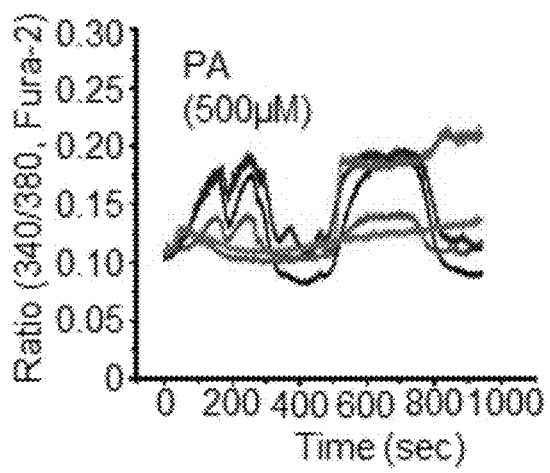

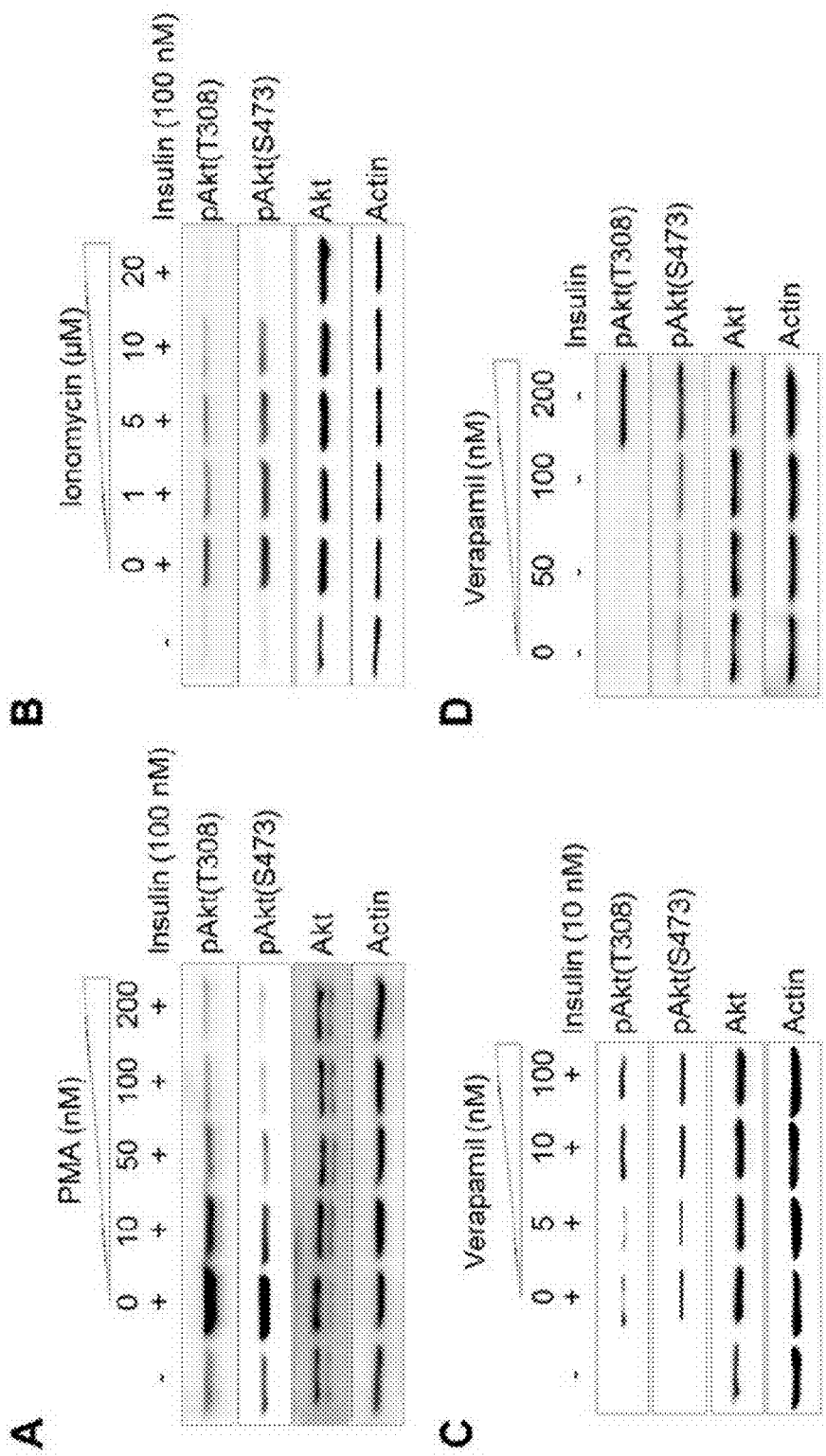
[Figure 4]

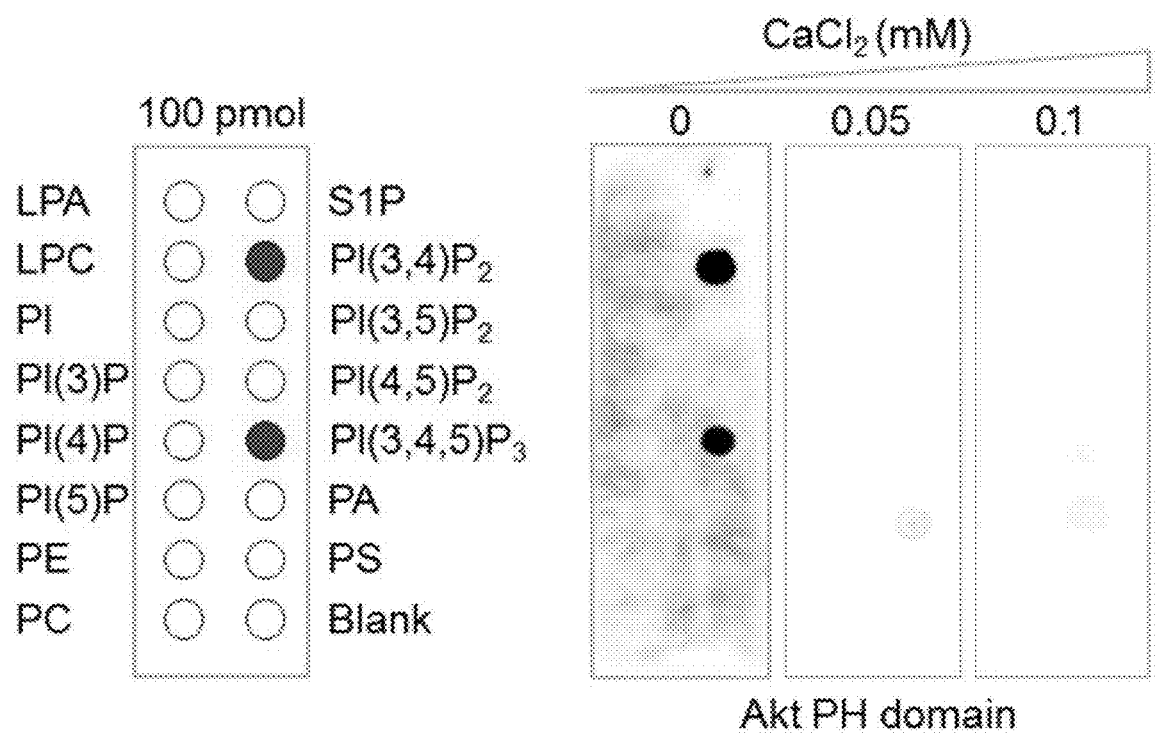
[Figure 5]

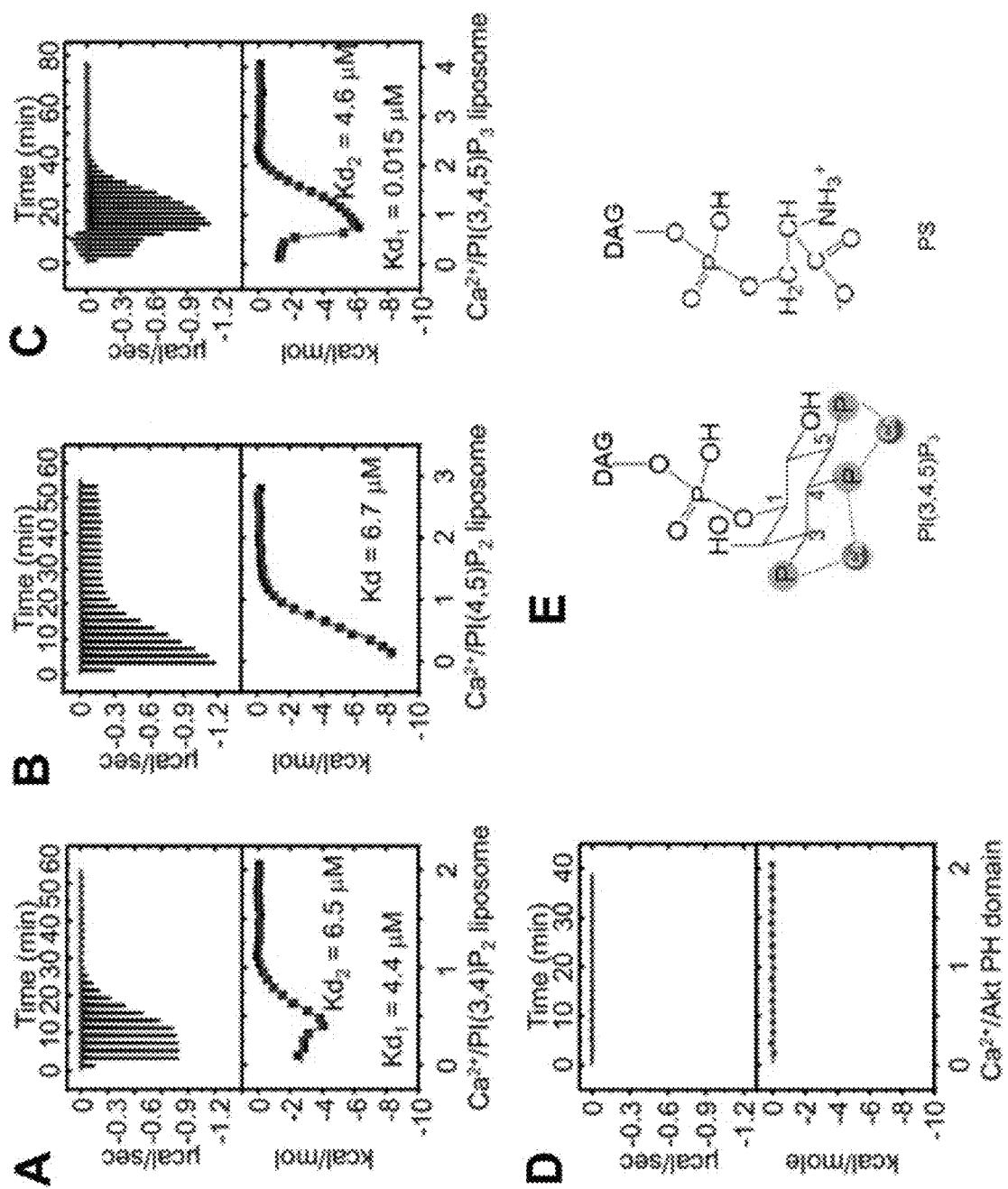
[Figure 6]

[Figure 7]
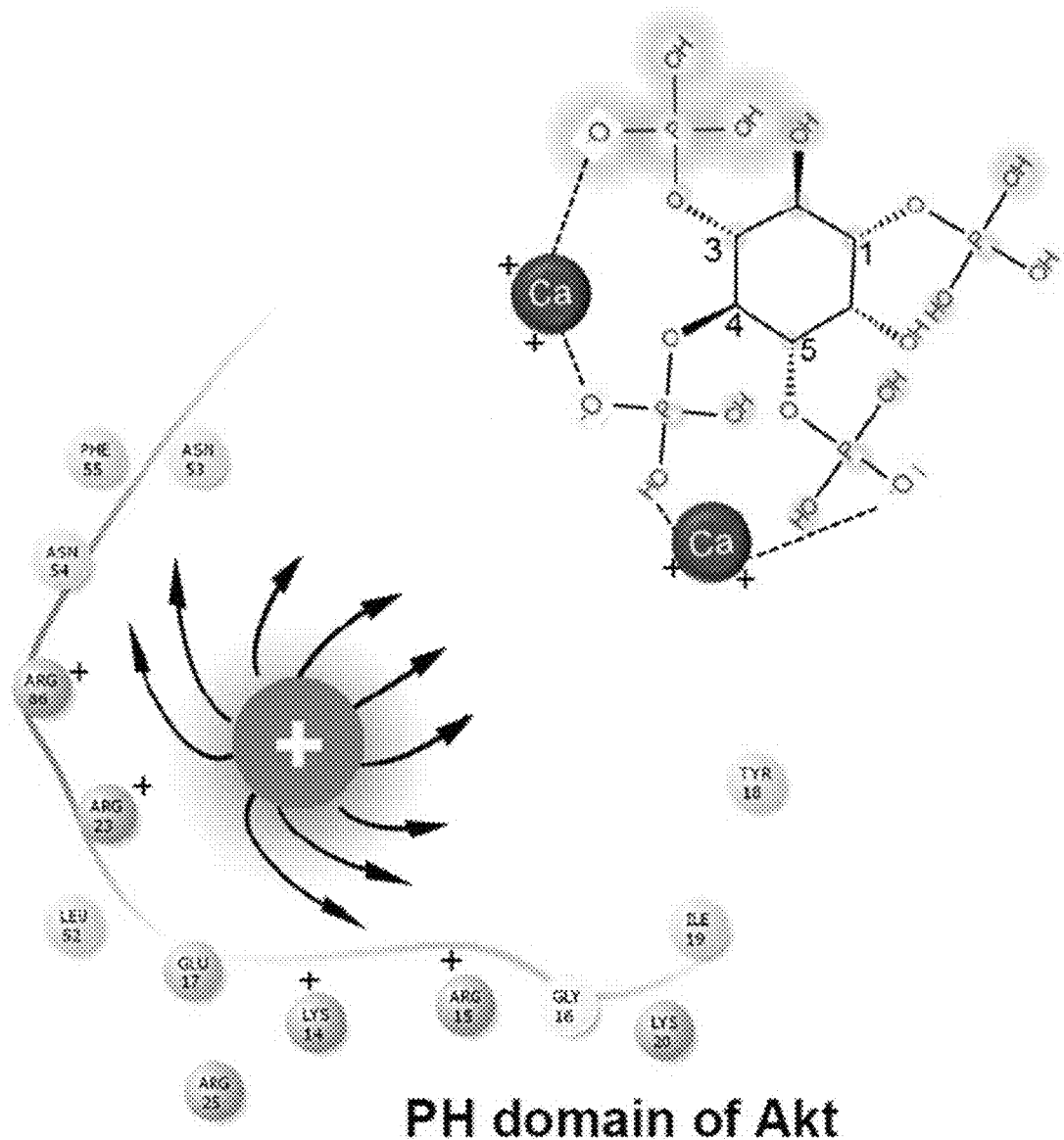

[Figure 8]
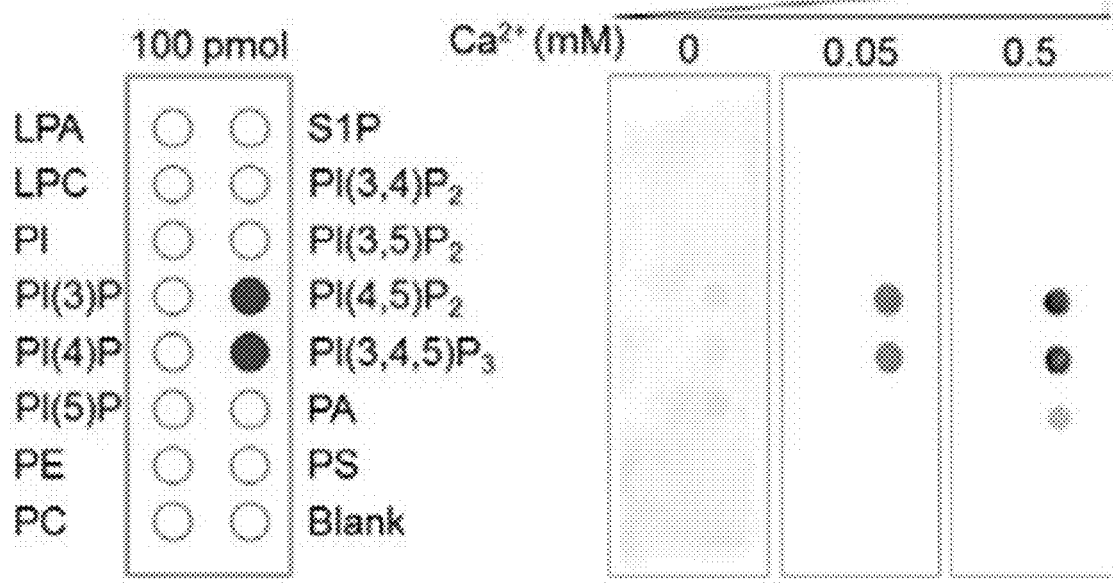
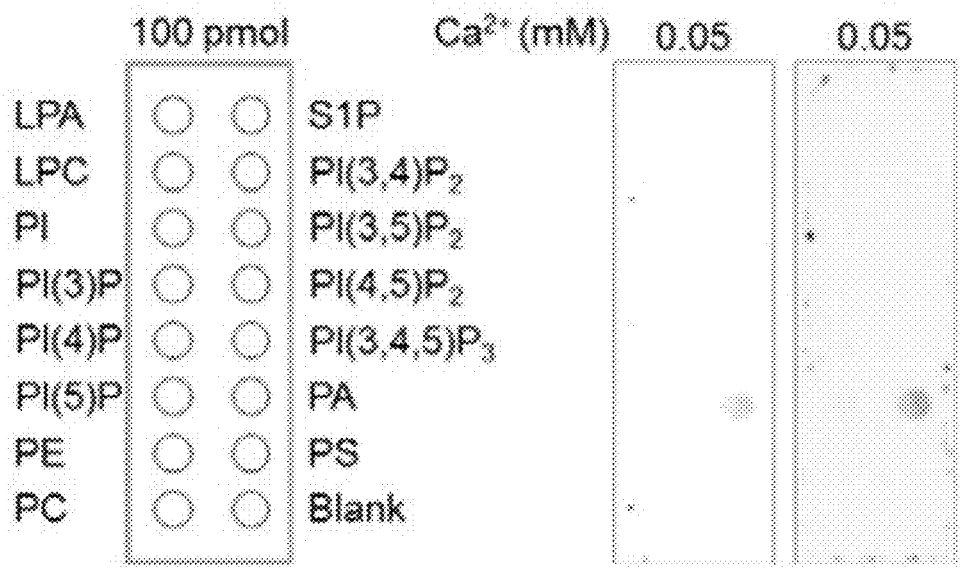

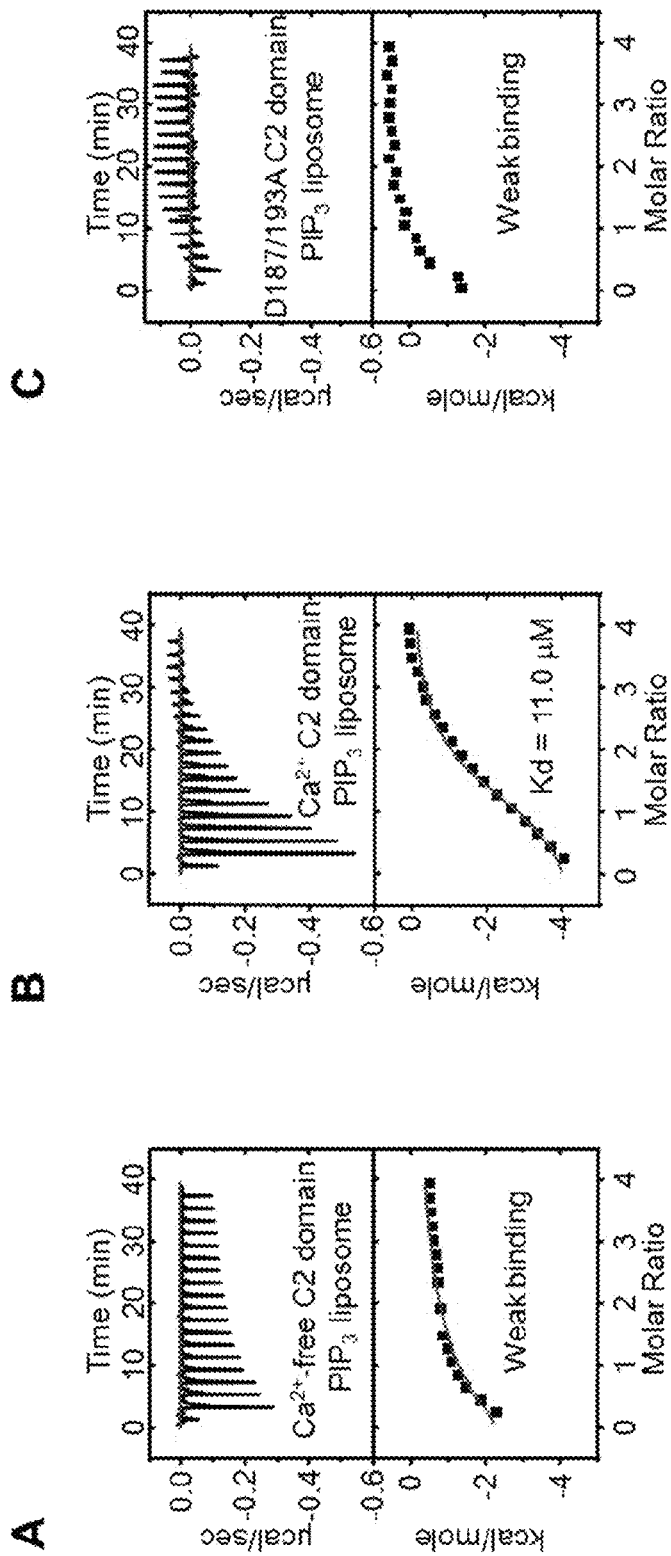
[Figure 9]

[Figure 10]
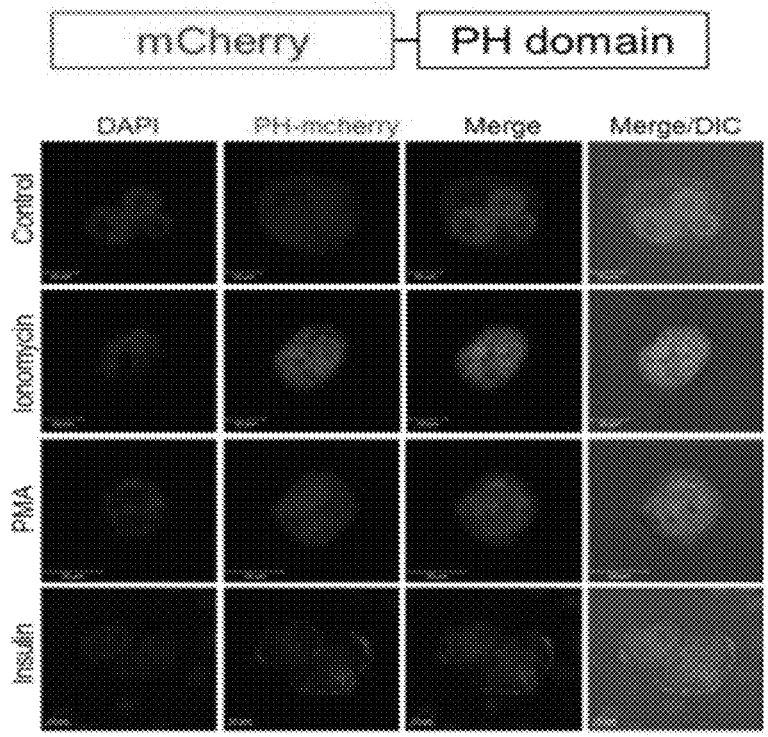
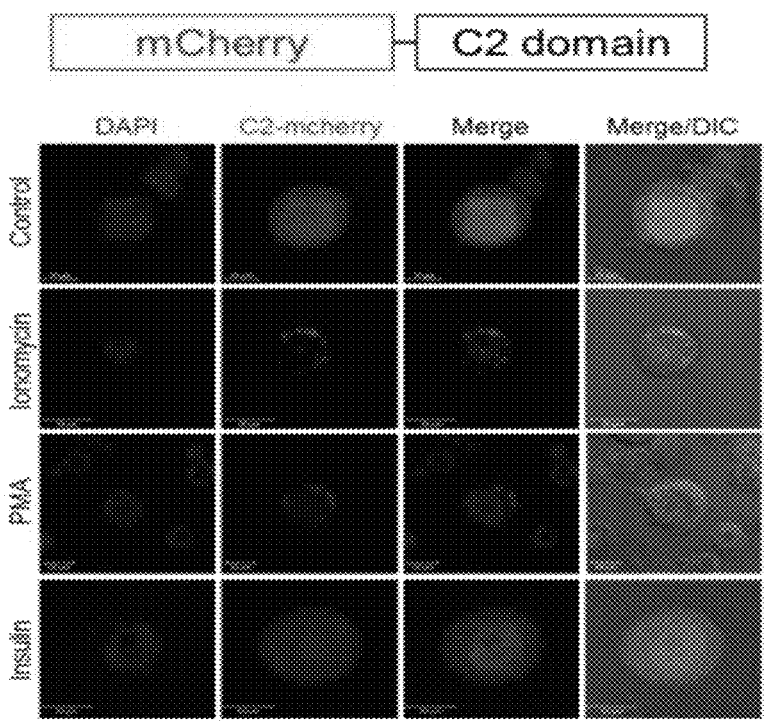

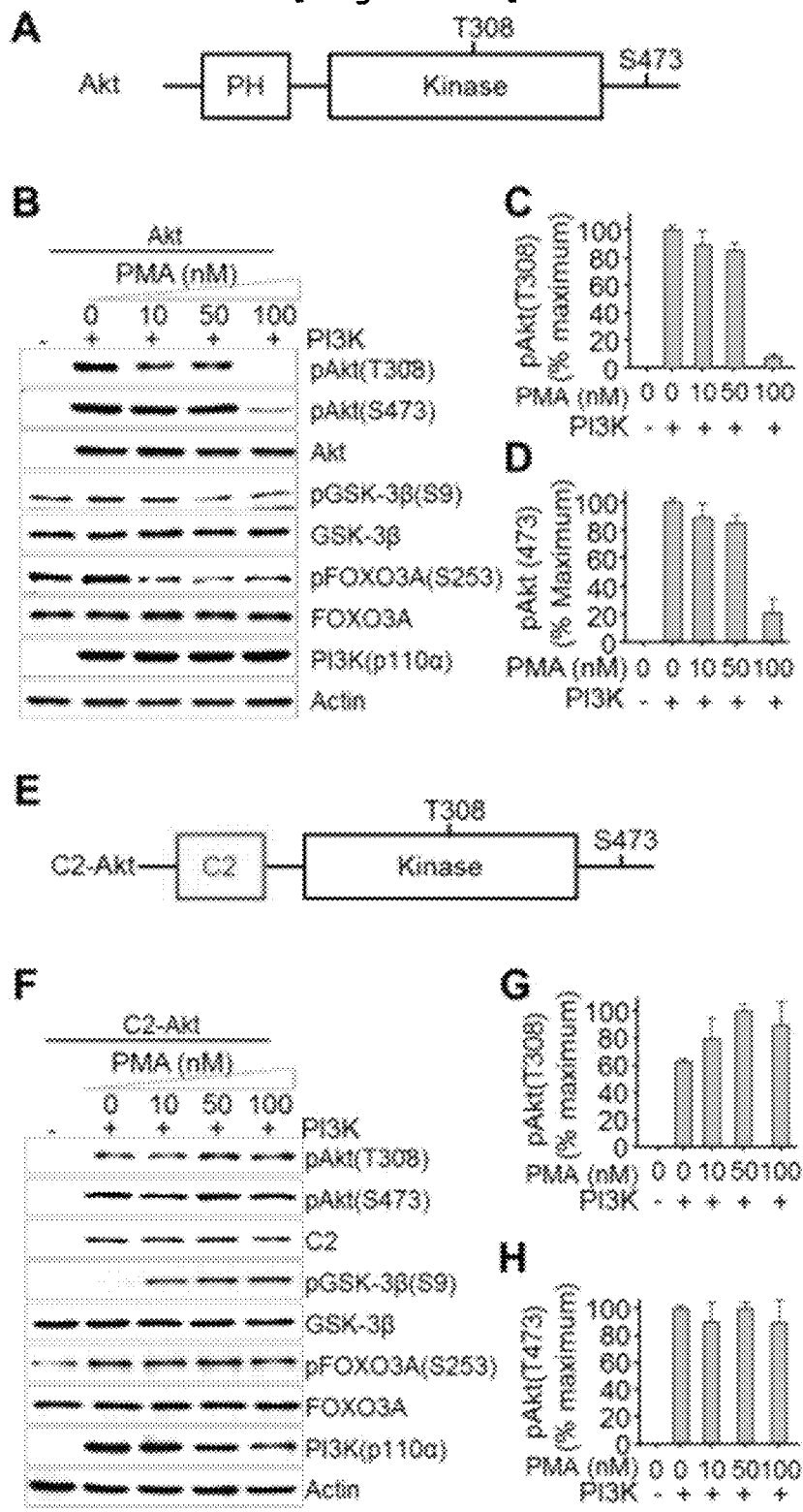
[Figure 11]

[Figure 12]
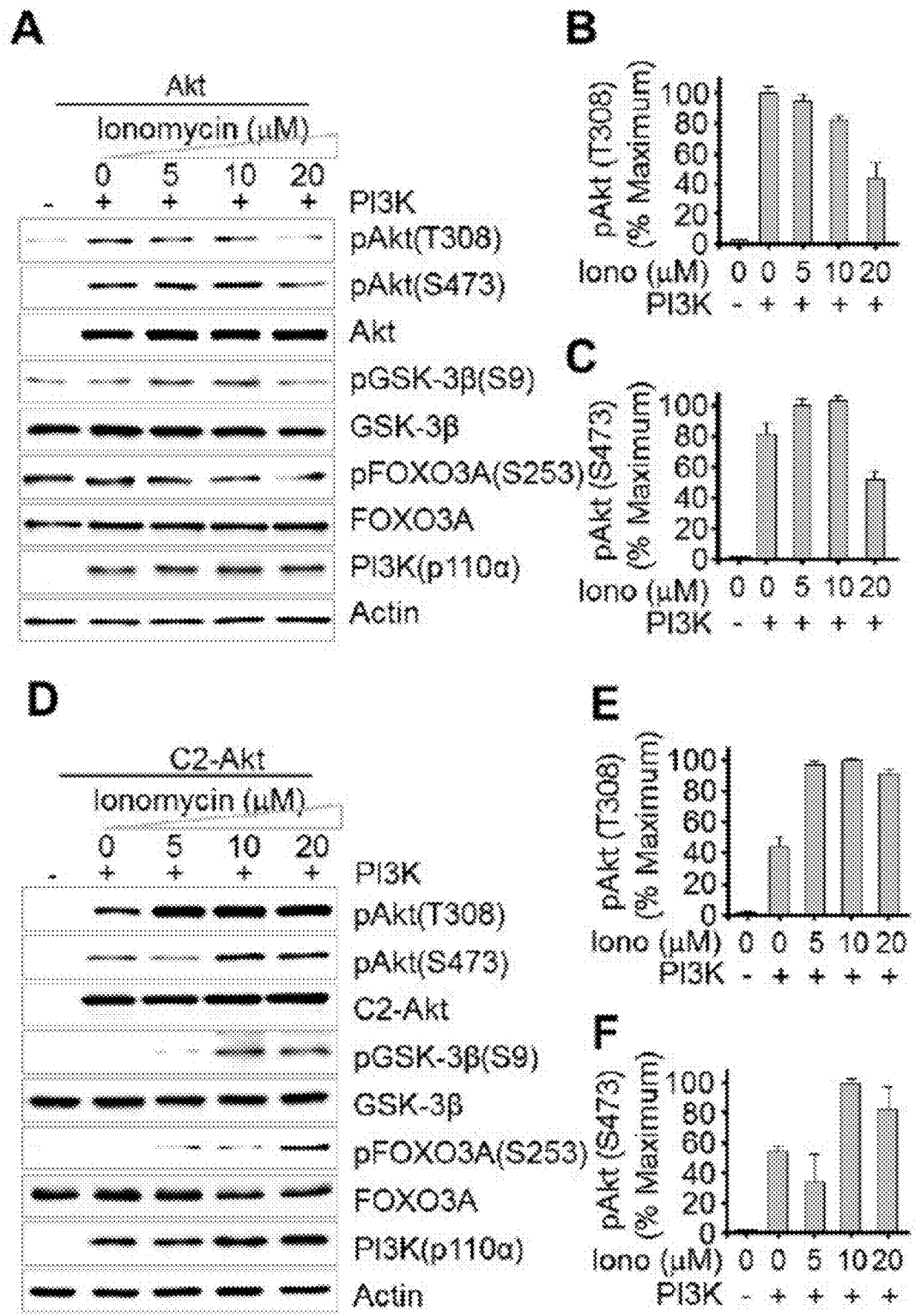

[Figure 13]
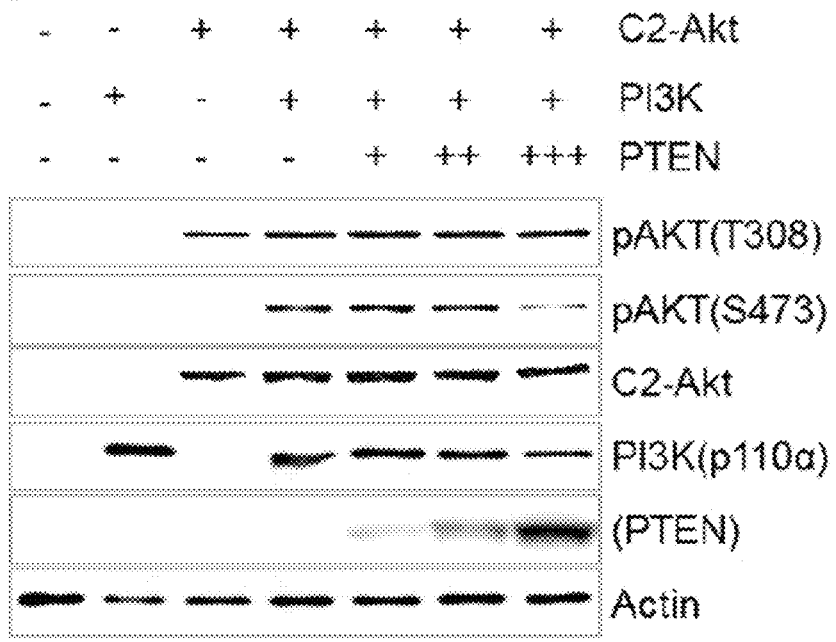
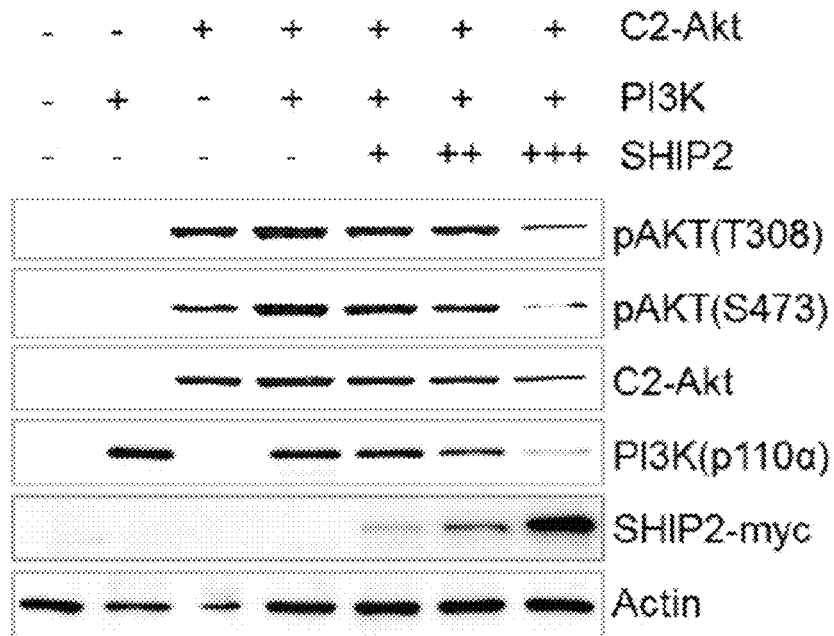

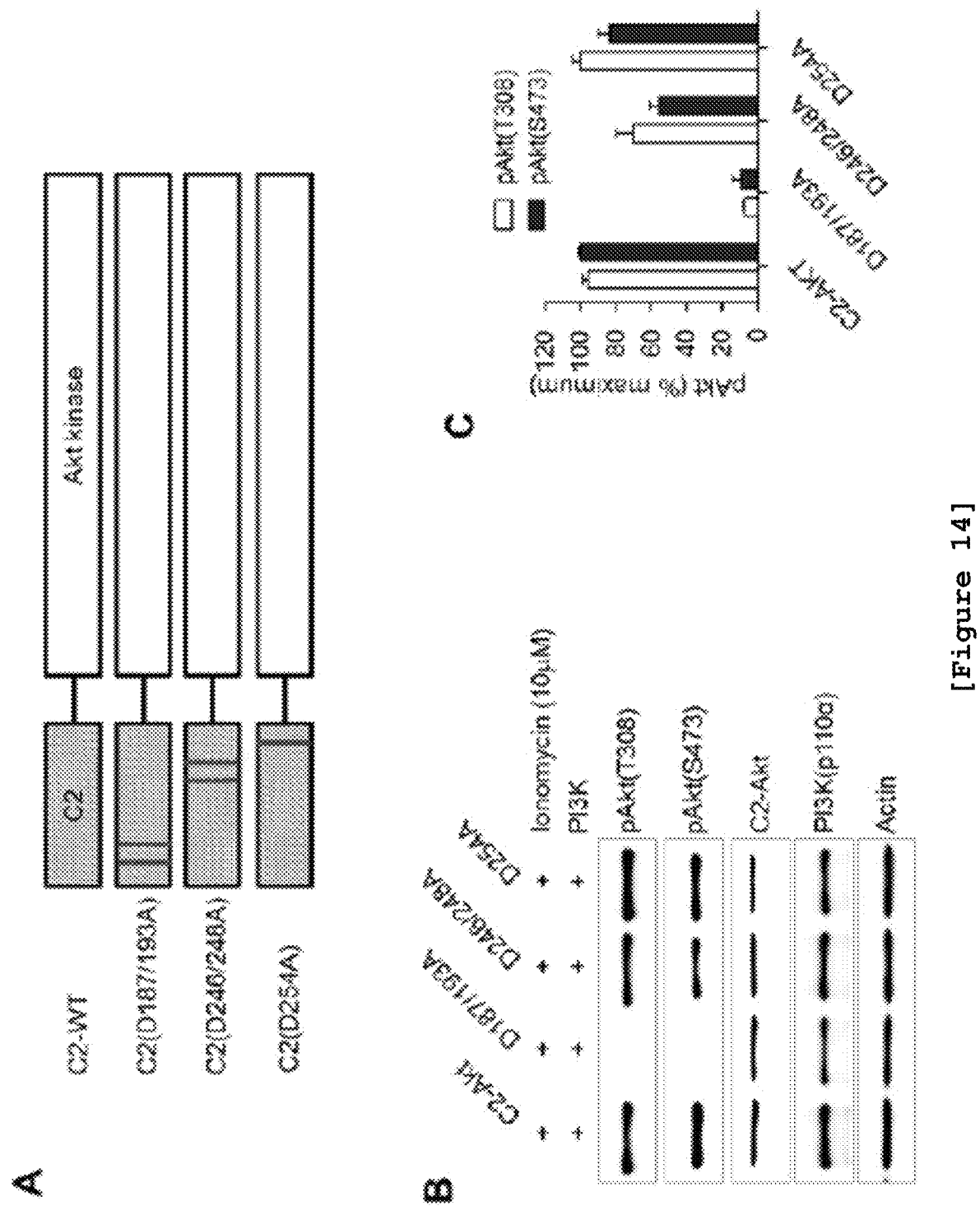
[Figure 14]

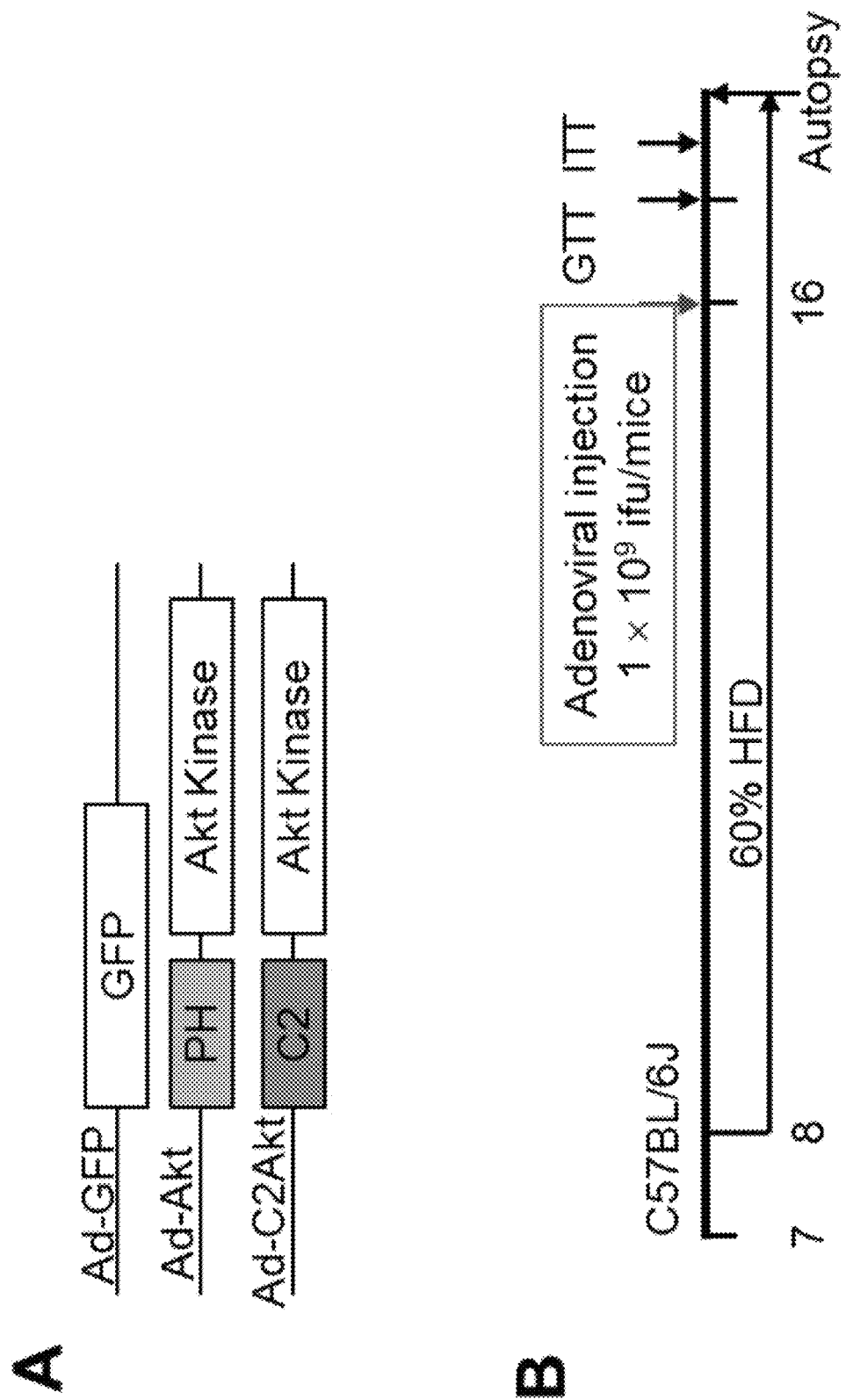
[Figure 15]

[Figure 16]
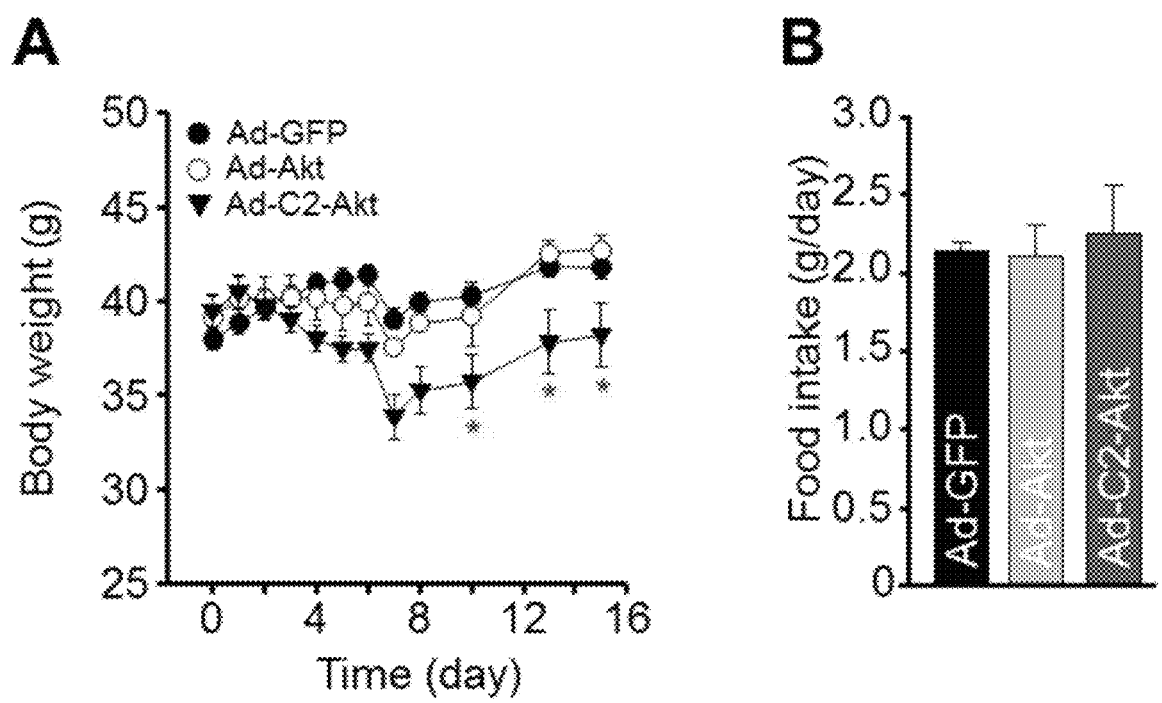

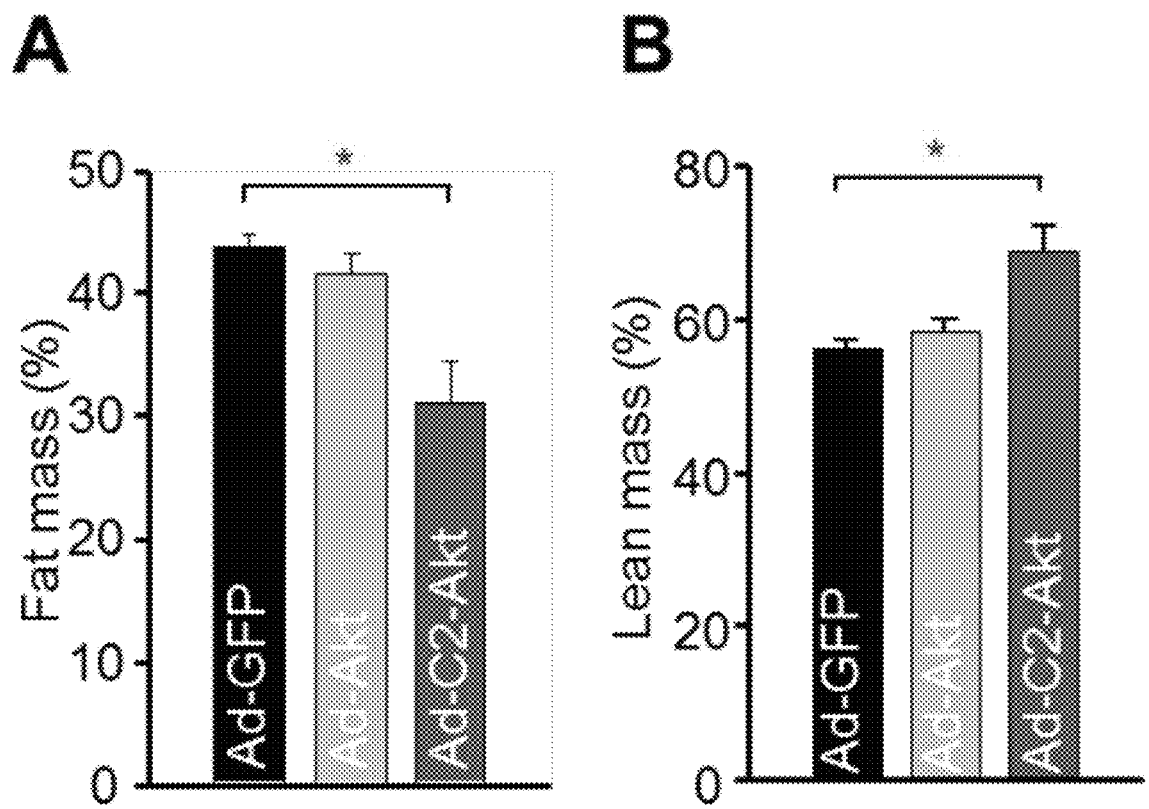
[Figure 17]

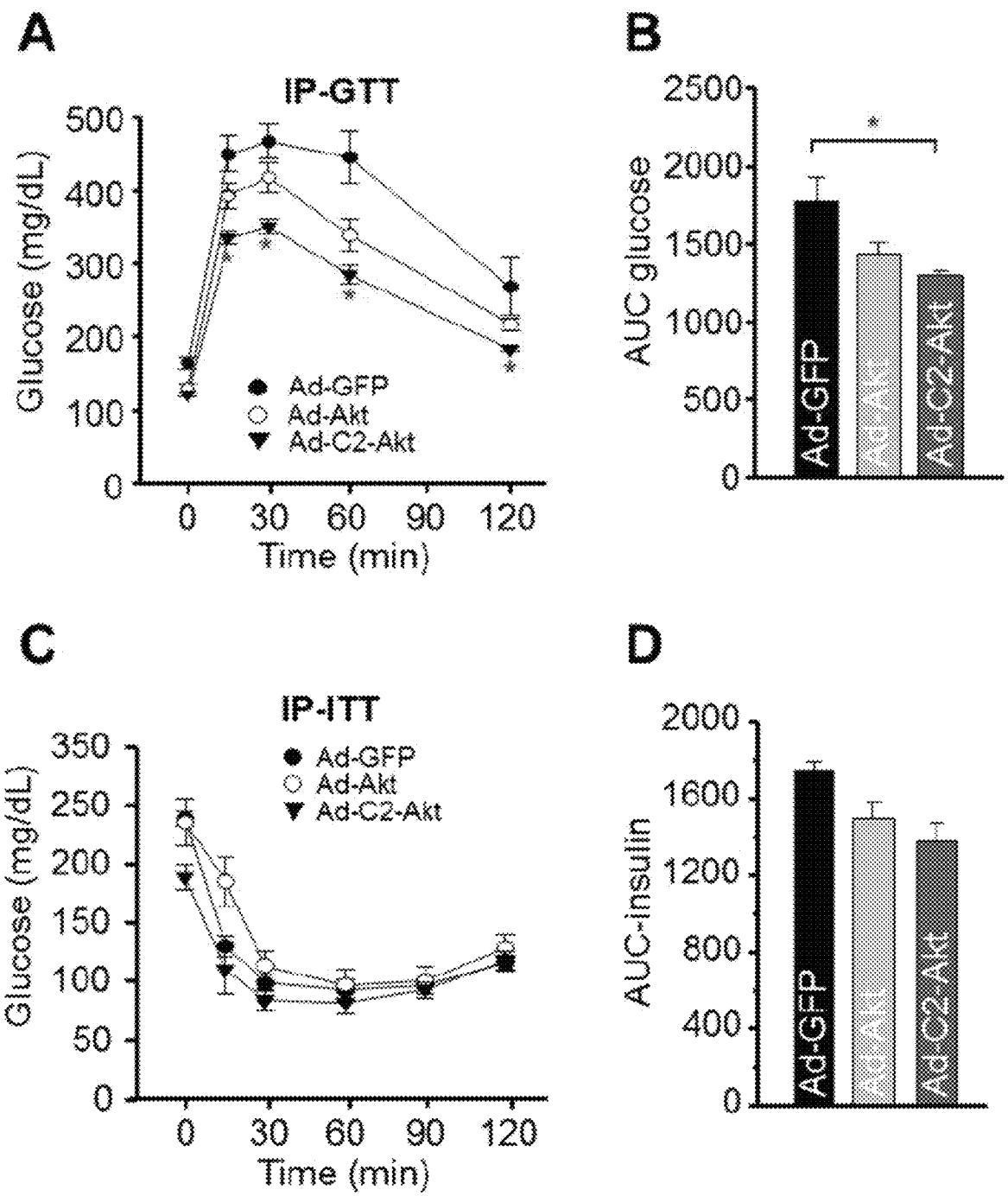
[Figure 18]

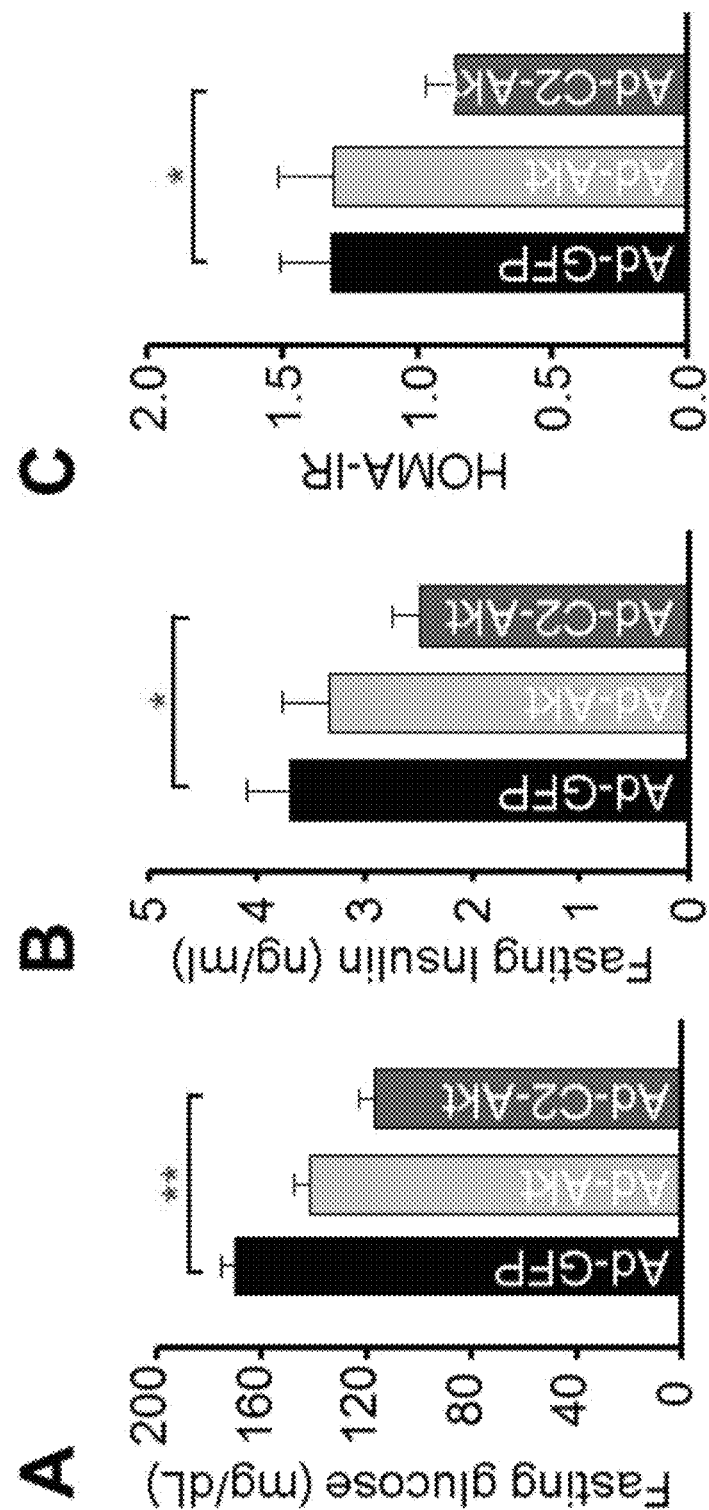
[Figure 19]

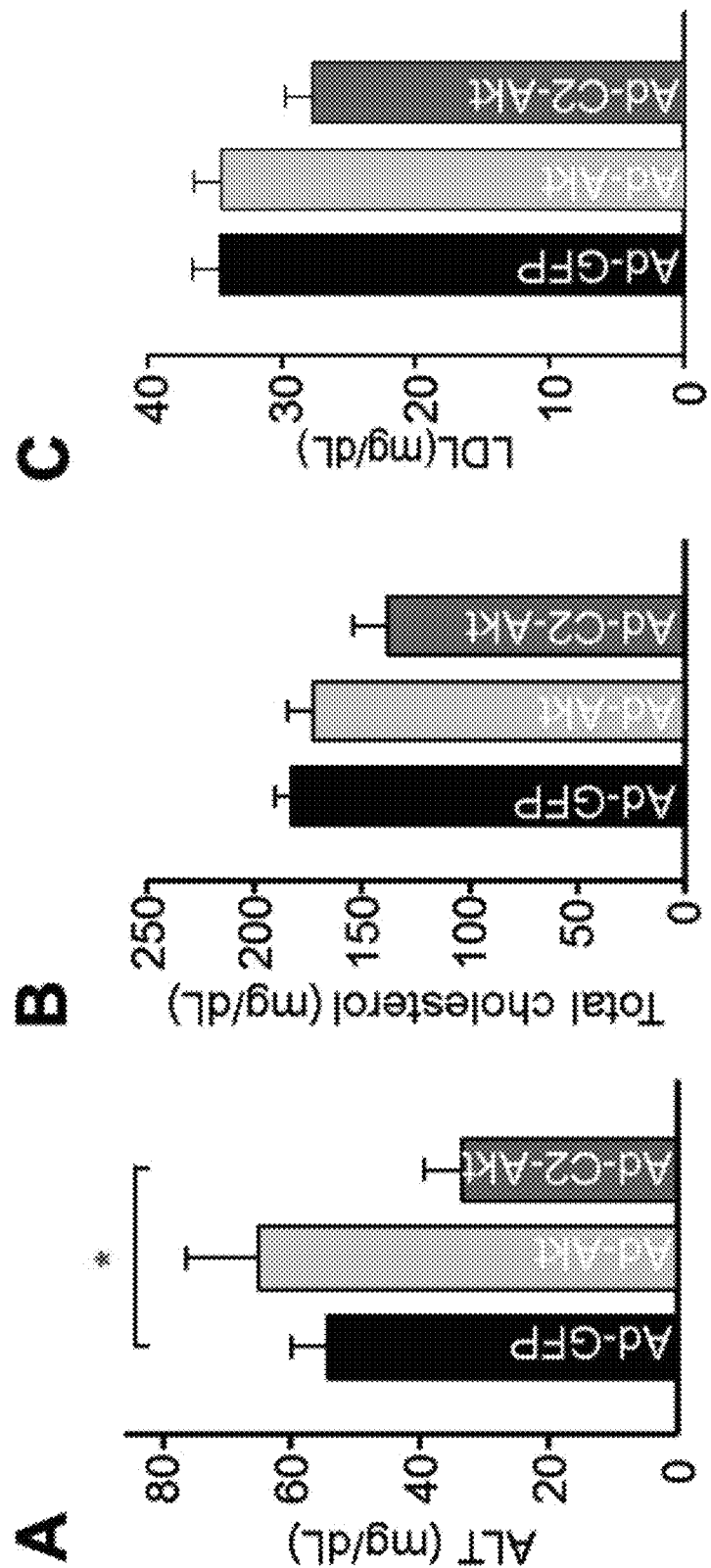
[Figure 20]

[Figure 21]
A
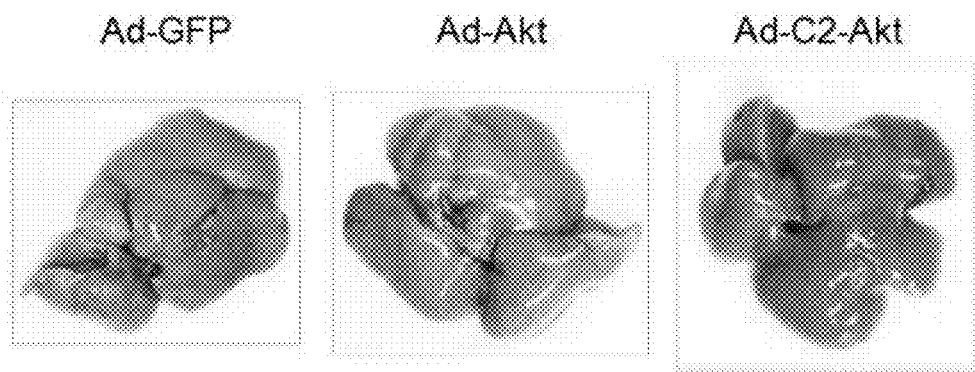
B
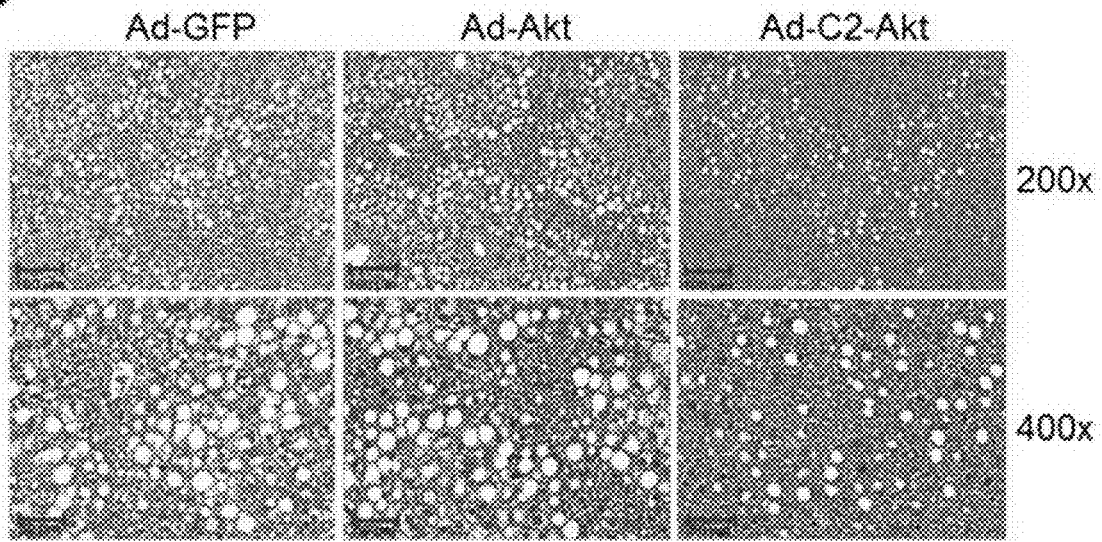

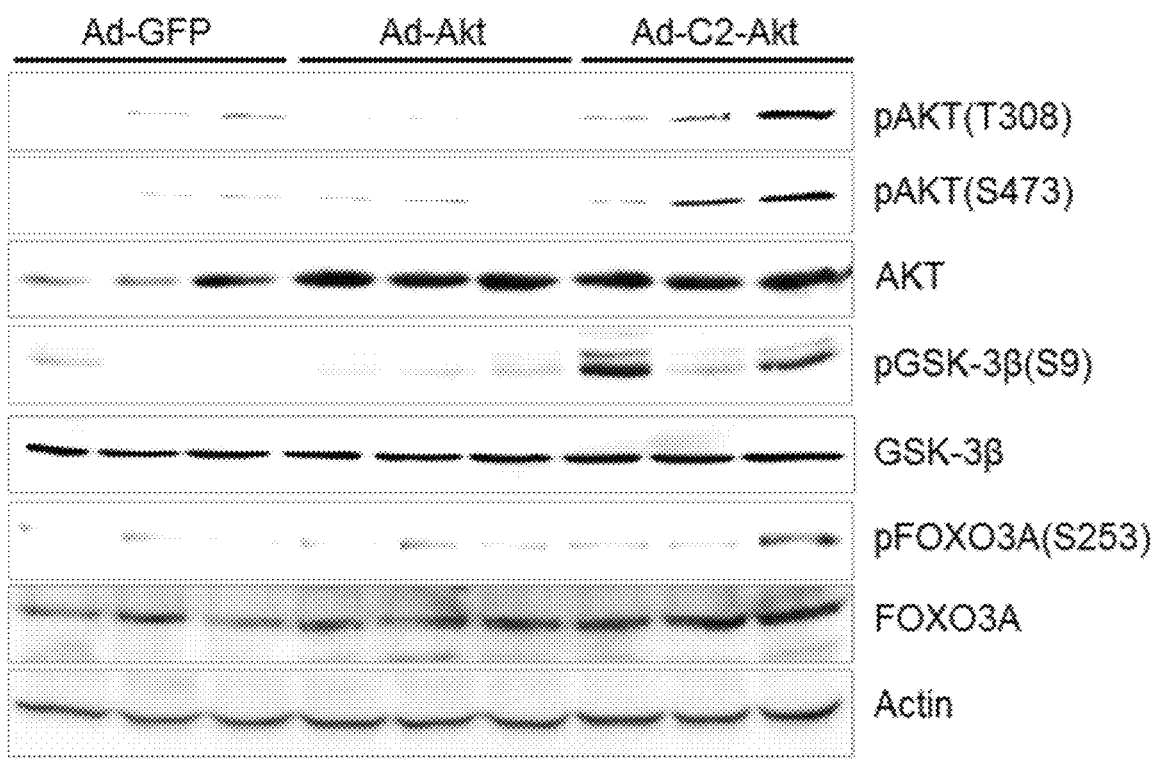
[Figure 22]

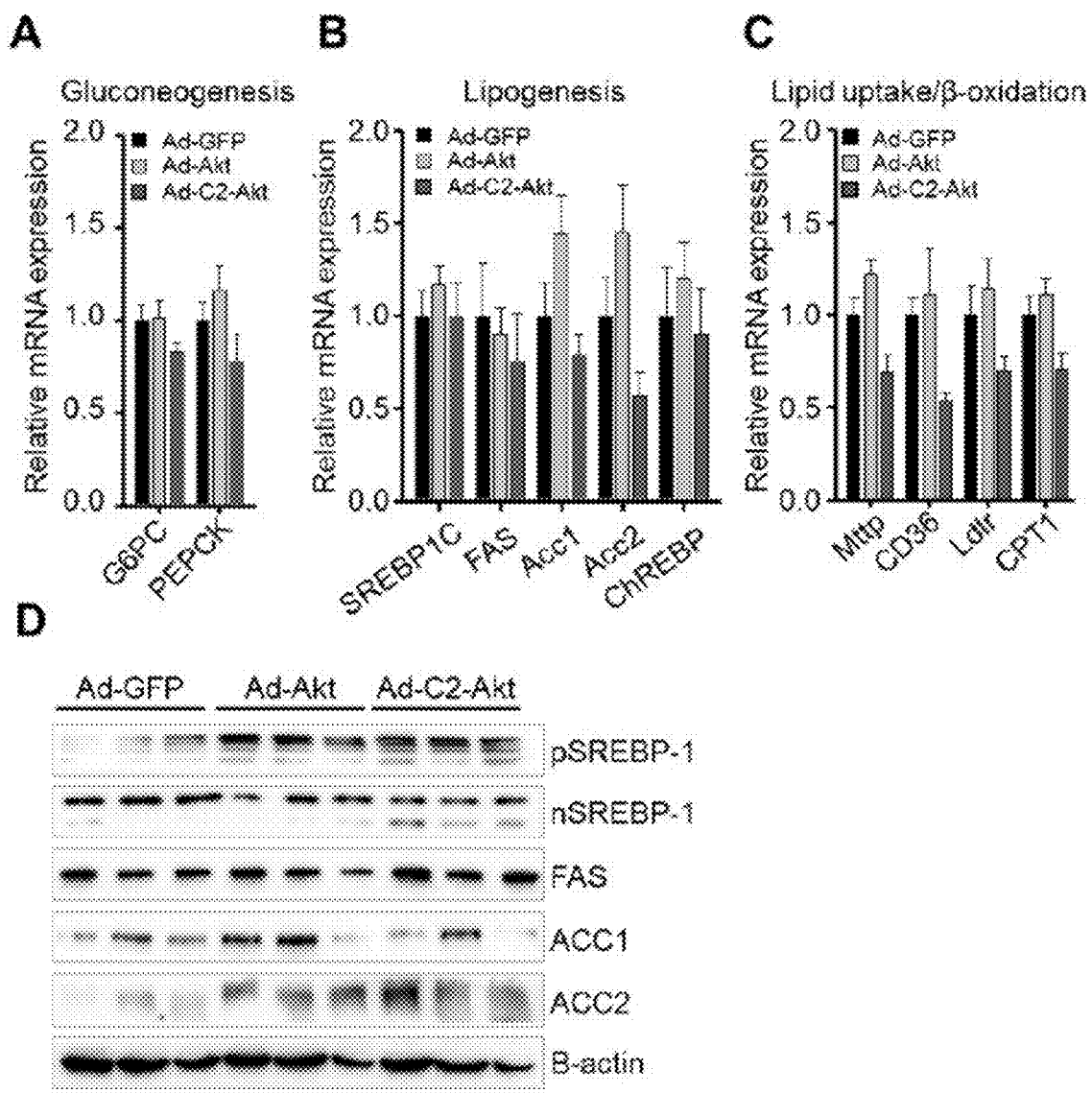
[Figure 23]

[Figure 24]
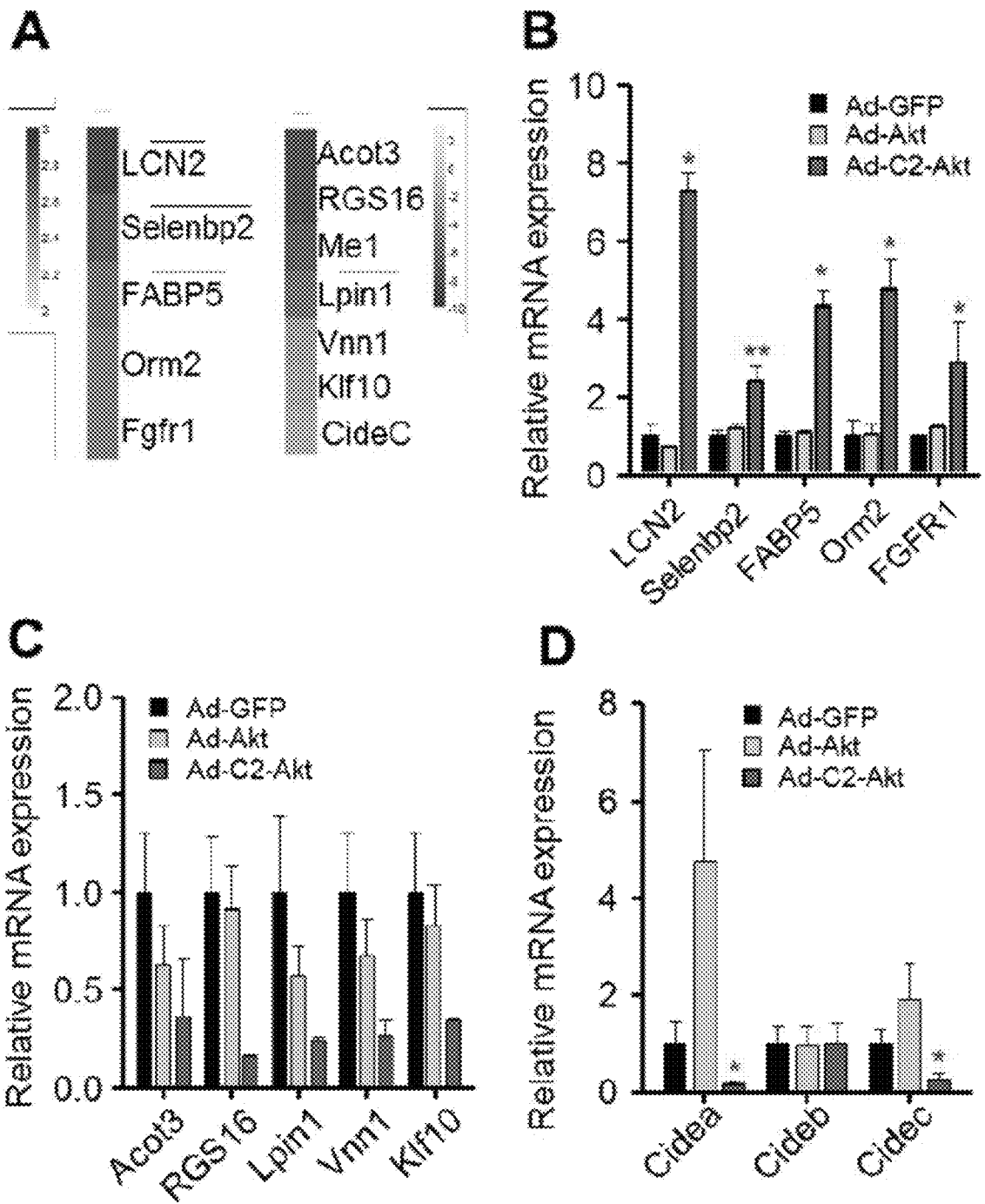

SCREENING METHOD OF DRUG CANDIDATES FOR TREATING DISEASE USING INTERACTION BETWEEN CALCIUM AND PHOSPHATIDYLINOSITOL PHOSPHATE

CROSS-REFERENCE TO RELATED APPLICATIONS

This application claims priority to Korean Patent Application Ser. No. 10-2017-0156849 filed Nov. 22, 2017, which is incorporated by reference herein in its entirety.

BACKGROUND OF THE INVENTION

1. Field of the Invention

The present invention relates to a method for screening drug candidates for treating a disease using the interaction between calcium and phosphatidylinositol phosphate.

2. Description of the Related Art

Metabolic disease is a disease caused when the metabolism of each organ of our body does not working smoothly. More precisely, metabolic disease is a generalized term for metabolic disorders caused by imbalance of glycosides, lipids, proteins, vitamins, minerals and moisture. In particular, at least 90% of adult disease is attributed to weakened immunity and lack of nutrition.

The representative metabolic diseases include obesity, diabetes, insulin resistance, hyperglycemia, hyperlipidemia, hypercholesterolemia, dyslipidemia and fatty liver. When fat is accumulated in the body due to metabolic diseases, insulin which is a hormone to send blood sugar to the liver or muscle is not properly generated, resulting in insulin resistance with displaying reduced insulin function. This causes an increase of blood sugar and atherosclerosis, resulting in the development of adult disease.

One of the metabolic diseases, diabetes is caused when the blood sugar which is absorbed enough in blood after meals is not absorbed in muscles and fat cells sufficiently. The unabsorbed glucose promotes the synthesis of glycogen, a storage form of glucose, but cannot inhibit the production of new glucose in the liver, which increases the concentration of blood sugar, resulting in hyperglycemia. Chronic diabetes can cause severe diabetic complications.

In the meantime, insulin resistance is caused when there is a mal-functioning in glucose migration and metabolism by insulin in fat cells and skeletal muscle, even though blood insulin concentration is still high. Insulin resistance does not inhibit the production of new glucose in the liver, leading to an increase in blood glucose concentration. Such functional defect is caused by abnormal insulin signaling in the tissues.

In general, the fat accumulated in muscles and liver tissues due to obesity increases intracellular calcium levels, which causes insulin resistance, a major cause of metabolic disorders such as diabetes. According to recent studies, saturated fatty acids inhibited calcium transport in the endoplasmic reticulum (ER) in the obesity or insulin resistance animal model, which resulted in the increase of calcium concentration in the cytoplasm. Such an increase in calcium concentration leads to an adverse effect on the functions of the organs such as ER and mitochondria, resulting in damage in metabolic homeostasis. However, the mechanism how excessive intracellular calcium concentration can cause insulin resistance has not been disclosed, yet.

Korean Patent Publication No. 10-2016-0139072 describes a pharmaceutical composition for treating metabolic disease, specifically obesity and type 2 diabetes, using a scab flower extract or a polyphenolic compound derived therefrom, Korean Patent Publication No. 10-2014-0039322 describes a method for treating metabolic disease such as hyperglycemia using fibroblast growth factor 19 (FGF 19) and fibroblast growth factor 21 (FGF21) having sugar educing activity.

Cancer is one of the diseases in which the number of patients is rapidly increasing world widely. Cancer has been treated by surgical operation, chemotherapy and radiotherapy. However, radiotherapy or surgical operation is only efficient in the early stage of cancer, but it is not efficient in the late stage of cancer. So, the late stage cancer can only be treated by chemotherapy. Chemotherapy is relatively easy to apply regardless of the stage of cancer, so it has attracted much attention, and various anticancer chemotherapeutic agents have been developed.

However, when such anticancer drugs are administered for a long term repeatedly or when cancer recurs, the cancer cells acquire resistance to the anticancer drugs so that the treatment effect thereof is not expected. Therefore, it is required to establish a screening method for anticancer drug candidates that can be used for chemotherapy through a novel mechanism.

Thus, the present inventors have tried to develop a method for screening drug candidates for treating diseases. In the course of our study, the inventors confirmed that the concentration of calcium was increased in the obesity induced insulin resistance animal model and the increased calcium concentration inhibited the migration of Akt protein containing PH domain to the cell membrane and the signal transduction thereof, while the protein containing C2 domain migrated to the cell membrane by interacting with calcium and PIP complex in the animal model above, leading to the completion of the present invention.

SUMMARY OF THE INVENTION

It is an object of the present invention to provide a method for screening drug candidates for treating a disease by using the interaction between calcium and phosphatidylinositol phosphate.

To achieve the above object, the present invention provides a method for screening drug candidates for treating metabolic disease comprising the steps of treating the cells having an increased intracellular calcium concentration with a test substance; investigating the interaction between calcium and phosphatidylinositol phosphate (PIP) in the cells having an increased intracellular calcium concentration; and selecting a test substance that can inhibit the interaction between calcium and PIP.

The present invention also provides a method for screening drug candidates for treating metabolic disease comprising the steps of treating a test substance to calcium and PIP mixture in vitro; investigating the interaction between calcium and PIP in the mixture above; and selecting a test substance that can inhibit the interaction between calcium and PIP.

The present invention also provides a method for screening drug candidates for treating cancer comprising the steps of treating a test substance to the cells; investigating the interaction between calcium and PIP in the cells above; and selecting a test substance that can increase the interaction between calcium and PIP.

The present invention also provides a method for screening drug candidates for treating cancer comprising the steps of treating a test substance to calcium and PIP mixture in vitro; investigating the interaction between calcium and PIP in the mixture above; and selecting a test substance that can increase the interaction between calcium and PIP.

The present invention also provides a method for screening drug candidates for treating hypertension comprising the steps of treating a test substance to the cells; investigating the interaction between calcium and PIP in the cells above; and selecting a test substance that can inhibit the interaction between calcium and PIP.

The present invention also provides a method for screening drug candidates for treating metabolic disease comprising the steps of treating a test substance to calcium and PIP mixture in vitro; investigating the interaction between calcium and PIP in the mixture above; and selecting a test substance that can inhibit the interaction between calcium and PIP.

Advantageous Effect

In the present invention, it was confirmed that the concentration of calcium was increased in the obesity induced insulin resistance animal model and the increased calcium concentration inhibited the migration of Akt protein containing PH domain and the signal transduction, while the protein containing C2 domain was able to migrate to the cell membrane by binding to calcium/PIP complex even under the condition of high calcium concentration. Therefore, the investigation of the interaction between calcium and PIP can be a useful method for screening of drug candidates for treating metabolic disease, cancer or hypertension.

BRIEF DESCRIPTION OF THE DRAWINGS

The application file contains at least one drawing executed in color. Copies of this patent application publication with color drawings will be provided by the Office upon request and payment of the necessary fee.

The application of the preferred embodiments of the present invention is best understood with reference to the accompanying drawings, wherein:

FIG. 1 is a series of diagrams, wherein (A of FIG. 1) is a set of fluorescence microscopic photographs showing that the intracellular calcium concentration in liver tissues of mice fed with high-fat diets (HFD) was increased compared to mice fed with normal diets (chow), (B of FIG. 1) is a graph showing the fluorescence intensity of the photograph, and (C of FIG. 1) is a set of photographs showing the results of Western blotting investigating the activity changes of the proteins involved in insulin signaling.

FIG. 2 is a series of diagrams, wherein (A of FIG. 2) is a set of fluorescence microscopic photographs showing that the intracellular calcium concentration was increased in the insulin resistance induced cells, (B of FIG. 2) is a graph showing the fluorescence intensity of the photograph, and (C of FIG. 2) is a set of photographs showing the results of Western blotting investigating the activity changes of the proteins involved in insulin signaling.

FIG. 3 is a set of graphs illustrating that the intracellular calcium concentration was increased by the treatment of PA in the insulin resistance induced cells.

FIG. 4 illustrates that the Akt protein phosphorylation was inhibited in the cells wherein the calcium concentration was increased by PMA (A of FIG. 4) or ionomycin (B of FIG. 4), while the Akt protein phosphorylation was increased in the cells wherein the calcium concentration was decreased by verapamil (C and D of FIG. 4).

FIG. 5 illustrates that the binding of the PH domain of the purified Akt protein to PI(3,4)$P_2$ or PI(3,4,5)$P_3$ was inhibited by increase of the calcium concentration, confirmed by protein-lipid binding assay.

FIG. 6 illustrates that the binding of the PH domain of the purified Akt protein to PI(3,4)$P_2$ (A of FIG. 6), PI(4,5)$P_2$ (B of FIG. 6), PI(3,4,5)$P_3$ (C of FIG. 6) or PS (D of FIG. 6, control) was inhibited by increase of the calcium concentration, confirmed by ITC (isothermal titration calorimetry), and the structures of calcium and PI(3,4,5)$P_3$ complex and PS (E of FIG. 6).

FIG. 7 is a schematic diagram illustrating that Akt protein PH domain was not combined with PI(3,4,5)$P_3$ under the condition of increased calcium concentration because calcium was combined with PI(3,4,5)$P_3$.

FIG. 8 illustrates that the binding of the C2 domain (A of FIG. 8) of PKCβ protein to PI(4,5)$P_2$ or PI(3,4,5)$P_3$ was promoted by increase of the calcium concentration, unlike the D187/193A and D246/248A mutant forms (B of FIG. 8) of the C2 domain of PKCβ protein, confirmed by protein-lipid binding assay.

FIG. 9 illustrates that the C2 domain (B of FIG. 9) of PKCβ protein was combined with PI(3,4,5)$P_3$ under the condition of increased calcium concentration, but the binding was not induced in the absence of calcium (A of FIG. 9), while the C2 domain mutant (C of FIG. 9) was not combined with PI(3,4,5)$P_3$, confirmed by ITC.

FIG. 10 is a set of photographs illustrating that the migration of the PH domain (A of FIG. 10) of Akt protein) in the cell membrane was inhibited by the increased calcium concentration, while the migration of the C2 domain (B of FIG. 10) in the cell membrane was promoted by the increased calcium concentration.

FIG. 11 shows that the activity of the wild-type Akt protein (A of FIG. 11) was inhibited under the condition of increased calcium concentration induced by the treatment of PMA, confirmed by Western blotting (B of FIG. 11), and the expression changes of pAkt(T308) (C of FIG. 11) and pAkt(T473) (D of FIG. 11) proteins; and that the Akt protein activity was increased by the C2-Akt fusion protein (E of FIG. 11) under the condition of increased calcium concentration, confirmed by Western blotting (F of FIG. 11), and the expression changes of pAkt(T308) (G of FIG. 11) and pAkt(T473) (H of FIG. 11) proteins.

FIG. 12 shows that the activity of the wild-type Akt protein was inhibited under the condition of increased calcium concentration induced by the treatment of PMA, confirmed by Western blotting (A of FIG. 12), and the expression changes of pAkt(T308) (B of FIG. 12) and pAkt(T473) (C of FIG. 12) proteins; and that the Akt protein activity was increased by the C2-Akt fusion protein under the condition of increased calcium concentration, confirmed by Western blotting (D of FIG. 12), and the expression changes of pAkt(T308) (E of FIG. 12) and pAkt(T473) (F of FIG. 12) proteins.

FIG. 13 shows the results of confirming the protein expression by treating PTEN (A of FIG. 13) or SHIP2 (B of FIG. 13), which was performed to determine whether PI(4,5)$P_2$ or PI(3,4,5)$P_3$ was more important in the signal transduction mechanism by the C2-Akt fusion protein.

FIG. 14 presents a schematic diagram (A of FIG. 14) illustrating the fusion protein prepared by using a mutant form of the C2 domain in the C2-Akt fusion protein; a diagram (B of FIG. 14) illustrating the results of Western blotting performed to identify an amino acid residue in the C2 domain that was able to increase the Akt protein activity by using the fusion protein above; and a graph (C of FIG. 14) illustrating the results of Western blotting above.

FIG. 15 is a set of schematic diagrams illustrating the structure of the adenovirus vector (A of FIG. 15) inserted in the animal model fed with high fat diet and the animal experiment plan (B of FIG. 15).

FIG. 16 is a set of graphs illustrating the weight loss (A of FIG. 16) and the changes in feed intake (B of FIG. 16) according to the treatment of the C2-Akt fusion protein in the animal model fed with high fat diet.

FIG. 17 is a set of graphs illustrating the fat reduction (A of FIG. 17) and the reduction of normal weight obesity (B of FIG. 17) by the C2-Akt fusion protein in the animal model fed with high fat diet.

FIG. 18 is a set of graphs illustrating the reduction of glucose levels (A and B of FIG. 18), the increase of insulin sensitivity (C of FIG. 18) and the decrease in fasting insulin levels (D of FIG. 18) according to the treatment of the C2-Akt fusion protein in the animal model fed with high fat diet.

FIG. 19 is a set of graphs illustrating the changes in fasting glucose (A of FIG. 19) and insulin (B of FIG. 19) levels in the animal model fed with high fat diet and the HOMA-IR (C of FIG. 19) calculated from the above values.

FIG. 20 is a set of graphs illustrating the ALT (A of FIG. 20), total cholesterol (B of FIG. 20) and LDL (C of FIG. 20) levels measured in the blood sample of the animal model fed with high fat diet.

FIG. 21 is a set of photographs illustrating the liver tissue (A of FIG. 21) of the animal model fed with high fat diet according to the treatment of the C2-Akt fusion protein and the reduction of lipid droplets in the liver tissue above (B of FIG. 21).

FIG. 22 is a set of photographs illustrating the results of Western blotting performed to confirm the Akt activity changes in the liver tissue of the high fat diet animal model treated with the C2-Akt fusion protein.

FIG. 23 is a set of graphs and photographs illustrating the expression changes of the genes involved in glucose production (A of FIG. 23), fat production (B of FIG. 23) and fat absorption (C of FIG. 23) in the liver tissue of the high fat diet animal model treated with the C2-Akt fusion protein and the expression changes (D of FIG. 23) of the proteins expressed by the genes.

FIG. 24 shows 5 types of genes up-regulated by the C2-Akt fusion protein and 7 types of genes (A of FIG. 24) down-regulated by the C2-Akt fusion protein; and the expression changes of the genes up-regulated above (B of FIG. 24), the genes down-regulated above (C of FIG. 24) and the genes that promote fatty liver (D of FIG. 24).

DESCRIPTION OF THE PREFERRED EMBODIMENTS

Hereinafter, the present invention is described in detail.

The present invention provides a method for screening drug candidates for treating metabolic disease comprising the steps of treating the cells having an increased intracellular calcium concentration with a test substance; investigating the interaction between calcium and phosphatidylinositol phosphate (PIP) in the cells having an increased intracellular calcium concentration; and selecting a test substance that can inhibit the interaction between calcium and PIP.

The said PIP above can be phosphatidylinositol (3,4,5)-triphosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

In the screening method of the present invention, the cells having an increased intracellular calcium concentration above can be an obesity cell model, an insulin resistance cell model, a diabetes cell model or a fatty liver cell model, and the candidate drugs screened by using the cell model above can be the candidate drugs to treat metabolic disease, particularly obesity, insulin resistance, diabetes or fatty liver.

In addition, the screening method of the present invention can include an additional step of selecting a test substance that can inhibit the migration of C2 domain to the cell membrane. The term "C2 domain" used in this invention indicates a protein structural domain involved in targeting a protein to the cell membrane. The C2 domain is generally either calcium dependent which is combined with 2 to 3 calcium ions or calcium independent which does not need calcium ions. The C2 domain has a β-sandwich consisting of 8β-strands that regulate calcium ions and the cavity formed by the first and last loops thereof is fused with phospholipids of the cell membrane.

The C2 domain is found in about 362 kinds of proteins, and 582 of them are known to exist (see, e.g., "http://" followed by "smart[dot]embl[dot]de/smart/do_annotation[dot]pl?DOMAIN=SM00239"). Particularly, the C2 domain can be originated from PI3K (phosphatidylinositol 3-kinase), PKC (protein kinase C), ABR (active breakpoint cluster region-related), BAIAP3 (BAI1-associated protein 3), BCR (breakpoint cluster region), C2CD2 (C2 calcium dependent domain containing 2), C2CD3 (C2 calcium dependent domain containing 3), CADPS (calcium-dependent secretion activator 1), CADPS2 (calcium-dependent secretion activator 2), CAPN5 (calpain-5), CAPN6 (calpain-6), CC2D1A (coiled-coil and C2 domain-containing protein 1A), CC2D1B (coiled-coil and C2 domain-containing protein 1B), CPNE1 (copine-1), CPNE2 (copine-2), CPNE3 (copine-3), CPNE4 (copine-4), CPNE5 (copine-5), CPNE6 (copine-6), CPNE7 (copine-7), CPNE8 (copine-8), CPNE9 (copine-9), DAB2IP (disabled homolog 2-interacting protein), DOC2A (double C2-like domain-containing protein alpha), DOC2B (double C2-like domain-containing protein beta), DYSF (dysferlin), ESYT1 (extended synaptotagmin-1), ESYT3 (extended synaptotagmin-3), FAM62B (extended synaptotagmin-2), FER1L3 (myoferlin), FER1L5 (fer-1 like family member 5), HECW1 (C2 and WW domain containing E3 ubiquitin protein ligase 1), HECW2 (C2 and WW domain containing E3 ubiquitin protein ligase 1), ITCH (itchy E3 ubiquitin protein ligase), ITSN1 (intersectin-1), ITSN2 (intersectin-2), MCTP1 (multiple C2 and transmembrane domain containing 1), MCTP2 (multiple C2 and transmembrane domain containing 2), MTAC2D1 (tandem C2 domains nuclear protein), NEDD4 (neural precursor cell expressed developmentally down-regulated protein 4), NEDD4L (neural precursor cell expressed developmentally down-regulated gene 4-like), OTOF (otoferlin), PCLO (protein piccolo), PIK3C2A (phosphatidylinositol-4-phosphate 3-kinase C2 domain-containing alpha), PIK3C2B (phosphatidylinositol-4-phosphate 3-kinase C2 domain-containing beta), PIK3C2G (phosphatidylinositol-4-phosphate 3-kinase C2 domain-containing gamma), PLA2G4A (cytosolic phospholipase A2), PLA2G4B (cytosolic phospholipase A2 beta), PLA2G4D(cytosolic phospholipase A2 delta), PLA2G4E (cytosolic phospholipase A2 epsilon), PLA2G4F (cytosolic phospholipase A2 zeta), PLCB1 (1-phosphatidylinositol-4,5-bisphosphate phosphodiesterase beta-1), PLCB2 (1-phosphatidylinositol-4,5-bisphosphate phosphodiesterase beta-2), PLCB3 (1-phosphatidylinositol-4,5-bisphosphate phosphodiesterase beta-3), PLCB4 (1-phosphatidylinositol-4,5-bisphosphate phosphodiesterase beta-4), PLCD1 (phospholipase C delta 1), PLCD3 (phospholipase C delta 3), PLCD4 (phospholipase C delta 4), PLCE1 (phospholipase C epsilon 1), PLCG1 (phospholipase C gamma 1), PLCG2 (phospholipase C gamma 2), PLCH1 (phospholipase C eta 1), PLCH2 (phospholipase C eta 2), PLCL1 (phospholipase C like 1), PLCL2 (phospholipase C like 2), PLCZ1 (phospholipase C zeta 1), PRF1 (perforin-1), PRKCA (protein kinase C alpha), PRKCB1 (protein kinase C beta type), PRKCE (protein kinase C epsilon), PRKCG (protein kinase C gamma), PRKCH (protein kinase C eta), RAB11FIP1 (Rab11 family-interacting protein 1), RAB11FIP2 (Rab11 family-interacting protein 2), RAB11FIP5 (Rab11 family-interacting protein 5), RASA1 (RAS p21 protein activator 1), RASA2 (RAS p21 protein activator 2), RASA3 (RAS p21 protein activator 3), RASA4 (RAS p21 protein activator 4), RASAL1 (RAS protein activator like 1), RASAL2 (RAS protein activator like 2), RGS3 (regulator of G-protein signaling 3), RIMS1 (regulating synaptic membrane exocytosis protein 1), RIMS2 (regulating synaptic membrane exocytosis protein 2), RIMS3 (regulating synaptic membrane exocytosis protein 3), RIMS4 (regulating synaptic membrane exocytosis protein 4), RPGRIP1 (X-linked retinitis pigmentosa GTPase regulator-interacting protein 1), RPH3A (rabphilin-3A), SMURF1 (E3 ubiquitin-protein ligase SMURF1), SMURF2 (E3 ubiquitin-protein ligase SMURF2), SYNGAP1 (synaptic Ras GTPase-activating protein 1), SYT1 (synaptotagmin-1), SYT10 (synaptotagmin-10), SYT11 (synaptotagmin-11), SYT12 (synaptotagmin-12), SYT13 (synaptotagmin-13), SYT14 (synaptotagmin-14), SYT15 (synaptotagmin-15), SYT16 (synaptotagmin-16), SYT17 (synaptotagmin-17), SYT2 (synaptotagmin-2), SYT3 (synaptotagmin-3), SYT4 (synaptotagmin-4), SYT5 (synaptotagmin-5), SYT6 (synaptotagmin-6), SYT7 (synaptotagmin-7), SYT8 (synaptotagmin-8), SYT9 (synaptotagmin-9), SYTL1 (synaptotagmin like 1), SYTL2 (synaptotagmin like 2), SYTL3 (synaptotagmin like 3), SYTL4 (synaptotagmin like 4), SYTL5 (synaptotagmin like 5), TOLLIP (toll interacting protein), UNC13A (Unc-13 homolog A), UNC13B (Unc-13 homolog B), UNC13C (Unc-13 homolog C), UNC13D (Unc-13 homolog D), WWC2 (WW and C2 domain containing 2), WWP1 (WW domain containing E3 ubiquitin protein ligase 1), WWP2 (WW domain containing E3 ubiquitin protein ligase 2) or PTEN (phosphatase and tensin homolog) protein.

In addition, the C2 domain can be a polypeptide consisting of any sequence known to those in this art. The polypeptide can include a mutant amino acid having different sequences or a fragment thereof produced by deletion, insertion and substitution of amino acid residues or a combination thereof, as long as such modification does not affect the protein function. Amino acid exchange in proteins or peptides that do not generally alter the activity of the molecule is well informed to those in the art. The polypeptide can be modified by phosphorylation, sulfation, acrylation, glycosylation, methylation, and farnesylation, etc. In a preferred embodiment of the present invention, the C2 domain can be a polypeptide consisting of the amino acid sequence represented by SEQ. ID NO: 14.

In addition, the screening method of the present invention can include an additional step of selecting a test substance that can promote the migration of Akt protein containing PH domain to the cell membrane. The term "Akt (protein kinase B) protein" used in this invention is a protein that plays an important role in the insulin signaling system mediated by $PI(3,4)P_2$ or $PI(3,4,5)P_3$. In particular, the Akt protein mediates downstream signal transduction by phosphorylating various proteins such as GSK3β (glycogen synthase kinase 3(3), AS160 (160 kDa substrate of Akt), and FOXO3 (the fork head transcription factor). The Akt protein has a pleckstrin homology (PH) domain consisting of approximately 120 amino acids at its N-terminus. This domain interacts directly with the cell membrane by binding to phosphatidylinositol phosphate (PIP).

The Akt protein can be derived from a mammal, particularly a human, a rat, a rabbit, a mouse, a sheep, a dog, and a pig, etc. In addition, the Akt protein can be a polypeptide consisting of any sequence known to those in the art, and can include a variant or a fragment thereof having the above-mentioned characteristics. In a preferred embodiment of the present invention, the Akt protein can be a polypeptide consisting of the amino acid sequence represented by SEQ. ID. NO: 16.

In a preferred embodiment of the present invention, the present inventors confirmed that the calcium concentration was increased in the obesity induced insulin resistance animal model and the increased calcium concentration inhibited the downstream signal transduction of Akt protein (see FIG. 1). These results were also the same in the cell model in which insulin resistance was induced (see FIG. 2).

The increased calcium was interacted with PIP existing on the cell membrane instead of Akt protein, by which the downstream signal transduction of Akt protein was inhibited (see FIG. 5 and FIG. 6). However, the C2 domain of PKCβ protein was interacted with PIP/calcium complex under the condition of increased calcium concentration, by which the migration of the C2 domain to the cell membrane was promoted (see FIG. 8 and FIG. 9).

Therefore, it was confirmed that a substance that inhibited the interaction between calcium and PIP in the cells having an increased intracellular calcium concentration can be used for the treatment of metabolic diseases.

The present invention also provides a method for screening drug candidates for treating metabolic disease comprising the steps of treating a test substance to calcium and PIP mixture in vitro; investigating the interaction between calcium and PIP in the mixture above; and selecting a test substance that can inhibit the interaction between calcium and PIP.

The said PIP can be phosphatidylinositol (3,4,5)-triphosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

The metabolic disease herein can be obesity, insulin resistance, diabetes or fatty liver.

In a preferred embodiment of the present invention, the present inventors confirmed that the calcium concentration was increased in the obesity induced insulin resistance animal model and the increased calcium concentration inhibited the downstream signal transduction of Akt protein (see FIG. 1). The increased calcium was interacted with PIP existing on the cell membrane instead of Akt protein, by which the downstream signal transduction of Akt protein was inhibited (see FIG. 5 and FIG. 6). However, the C2 domain of PKCβ protein was interacted with PIP/calcium complex under the condition of increased calcium concentration, by which the migration of the C2 domain to the cell membrane was promoted (see FIG. 8 and FIG. 9).

Therefore, it was confirmed that a substance that can inhibit the interaction between calcium and PIP can be used for the treatment of metabolic diseases.

The present invention also provides a method for screening drug candidates for treating cancer comprising the steps of treating a test substance to the cells; investigating the interaction between calcium and PIP in the cells above; and selecting a test substance that can increase the interaction between calcium and PIP.

The said PIP can be phosphatidylinositol (3,4,5)-triphosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

The screening method of the present invention can additionally include one or more steps selected from the group consisting of the step of selecting a test substance that can inhibit the migration of Akt protein to the membrane and the step of selecting a test substance that can inhibit the signal transduction of Akt protein. The Akt protein can be characterized by the description above, and particularly it can be a polypeptide consisting of the amino acid sequence represented by SEQ. ID. NO: 16.

It is generally known that Akt protein is over-expressed in cancer cells and phosphorylation is induced at the 308$^{th}$ tyrosine and the 473$^{rd}$ serine of the protein. The phosphorylation increases the interaction between Akt protein and PIP, so that a substance that can increase the interaction between PIP and calcium instead of Akt protein can be selected as a drug candidate for treating cancer.

In a preferred embodiment of the present invention, the present inventors confirmed that the calcium concentration was increased in the obesity induced insulin resistance animal model and the increased calcium concentration inhibited the downstream signal transduction of Akt protein (see FIG. 1). The increased calcium was interacted with PIP existing on the cell membrane instead of Akt protein, by which the downstream signal transduction of Akt protein was inhibited (see FIG. 5 and FIG. 6). However, the C2 domain of PKCβ protein was interacted with PIP/calcium complex under the condition of increased calcium concentration, by which the migration of the C2 domain to the cell membrane was promoted (see FIG. 8 and FIG. 9).

Therefore, it was confirmed that a substance that can promote the interaction between calcium and PIP can be used for the treatment of cancer.

The present invention also provides a method for screening drug candidates for treating cancer comprising the steps of treating a test substance to calcium and PIP mixture in vitro; investigating the interaction between calcium and PIP in the mixture above; and selecting a test substance that can increase the interaction between calcium and PIP.

The said PIP can be phosphatidylinositol (3,4,5)-triphosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

In a preferred embodiment of the present invention, the present inventors confirmed that the calcium concentration was increased in the obesity induced insulin resistance animal model and the increased calcium concentration inhibited the downstream signal transduction of Akt protein (see FIG. 1). The increased calcium was interacted with PIP existing on the cell membrane instead of Akt protein, by which the downstream signal transduction of Akt protein was inhibited (see FIG. 5 and FIG. 6). However, the C2 domain of PKCβ protein was interacted with PIP/calcium complex under the condition of increased calcium concentration, by which the migration of the C2 domain to the cell membrane was promoted (see FIG. 8 and FIG. 9).

Therefore, it was confirmed that a substance that can promote the interaction between calcium and PIP can be used for the treatment of cancer.

The present invention also provides a method for screening drug candidates for treating hypertension comprising the steps of treating a test substance to the cells; investigating the interaction between calcium and PIP in the cells above; and selecting a test substance that can inhibit the interaction between calcium and PIP.

The said PIP can be phosphatidylinositol phosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

The screening method of the present invention can additionally include one or more steps selected from the group consisting of the step of selecting a test substance that can inhibit the migration of Akt protein to the membrane and the step of selecting a test substance that can inhibit the signal transduction of Akt protein. The Akt protein can be characterized by the description above, and particularly it can be a polypeptide consisting of the amino acid sequence represented by SEQ. ID. NO: 16.

In a preferred embodiment of the present invention, the present inventors confirmed that when verapamil used as a therapeutic agent for hypertension was treated to the cells having an increased intracellular calcium concentration, the increased calcium concentration was inhibited and the phosphorylation of Akt protein was increased (see FIG. 4).

So, the substance that can increase the phosphorylation of Akt by inhibiting the increase of intracellular calcium concentration can be selected as a drug candidate for treating hypertension. Therefore, the substance that can inhibit the interaction between calcium and PIP can be used for the treatment of hypertension.

In addition, the present invention provides a method for screening drug candidates for treating metabolic disease comprising the steps of treating a test substance to calcium and PIP mixture in vitro; investigating the interaction between calcium and PIP in the mixture above; and selecting a test substance that can inhibit the interaction between calcium and PIP.

The said PIP can be phosphatidylinositol (3,4,5)-triphosphate, phosphatidylinositol (3.4)-bisphosphate or phosphatidylinositol (4,5)-bisphosphate. In the screening method of the present invention, the interaction between calcium and PIP can be investigated by any conventional method well known to those in the art, and particularly one or more methods can be selected from the group consisting of ITC (isothermal titration calorimetry) and protein-lipid binding assay.

In a preferred embodiment of the present invention, the present invention confirmed that when verapamil being used for the treatment of hypertension was treated to the cells having an increased calcium concentration, the increased calcium concentration was reduced and the phosphorylation of Akt protein was increased (see FIG. 4).

From the above results, it was confirmed that a substance that can increase the phosphorylation of Akt protein by suppressing the increase of intracellular calcium concentration would be selected as a drug candidate for treating hypertension. Therefore, the substance that can inhibit the interaction between calcium and PIP can be used for the treatment of hypertension.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Confirmation of Increased Calcium Level in Obesity Induced Insulin Resistance Animal Model The following experiment was performed in order to confirm the changes of intracellular calcium concentration in liver cells of the insulin resistance animal model induced by obesity.

First, male C57BL/6 mice at 8 weeks (Orient Bio, Korea) were raised in an animal facility of Lee Gil Ya Cancer and Diabetes Institute (Gachon University, Korea). Particularly, the mice were raised in a sterile chamber at the temperature of 23±1° C. with 12 hr/12 hr light/dark cycle, and free dietary environment. At this time, the mice were divided into the fasted group wherein the mice were fasted for 16 hours and the refed group wherein the mice were fasted for 16 hours and then fed for 4 hours. Each group was sub-divided into the high fat diet group (HFD) and the normal diet group (chow). The high fat diet group (HFD) mice were fed with diet containing 60% fat, while the normal diet group (chow) mice were fed with diet containing 10% fat. 8 weeks later, the mice were anesthetized and the liver was perfused by using buffer 1 (142 mM NaCl, 6.7 mM KCl, 10 mM HEPES and 2.5 mM EGTA, pH 7.4). Buffer 1 above was replaced with buffer 2 (0.5 mg/Mg collagen, 66.7 mM NaCl, 6.7 mM KCl, 10 mM HEPES and 4.8 mM CaCl, pH 7.6), and then the perfused liver was extracted. The extracted liver was washed and degraded by using Percoll cushion gradient. The degraded cells were suspended and cultured in Hepatozyme-SFM (Gibco-BRL USA) culture medium supplemented with 10% FBS and 1% antibiotics and antifungal agent. The prepared cells were diluted in DMEM at the density of $1 \times 10^7$ cells/Mg, to which 4 μM Fluo-3 AM (Invitrogen, USA) was added. The cells were reacted at 37° C. for 45 minutes and then fixed with 4% paraformaldehyde for 10 minutes. The fixed cells were washed with PBS twice for 5 minutes each time and dried, followed by mounting by using 4,6-diamidino-2-phenylindole. The mounted cells were analyzed using a fluorescence microscope (Zeiss Axioplan 2). The results are shown in FIG. 1A and FIG. 1B.

As shown in FIG. 1A and FIG. 1B, the intracellular calcium level was significantly increased in the liver tissues of the mouse fed with high fat diet 4 times, compared with the mouse fed with normal diet (FIG. 1A and FIG. 1B).

EXAMPLE 2

Confirmation of Inhibition of Insulin Signaling in Obesity Induced Insulin Resistance Animal Model To investigate the insulin sensitivity in the liver cells of the insulin resistance animal model induced by obesity, the expression patterns of the proteins involved in Akt protein phosphorylation mechanism were confirmed by Western blotting.

First, male C57BL/6 mice at 8 weeks were divided into the fasted group wherein the mice were fasted for 16 hours and the refed group wherein the mice were fasted for 16 hours and then fed for 4 hours. Each group was sub-divided into the high fat diet group (HFD) and the normal diet group (chow). The liver cells were extracted from the raised mice by the same manner and under the same conditions as described in Example 1. The extracted liver cells were lysed in a lysis buffer containing phosphatase (Sigma-Aldrich, USA) and protease inhibitor (Sigma-Aldrich, USA). Proteins extracted from 2 to 3 mg of the liver tissue were homogenized by using a tissue homogenizer (TissuLyser, Qiagen, USA) for 1.5 minutes at a frequency of 1/30 sec. The homogenized lysate was centrifuged at 12,000 rpm for 15 minutes and the supernatant was obtained. The amount of the extracted protein was quantified by using a protein assay kit (Bio-Rad Laboratories, USA), and at this time BSA was used as a standard sample. 3 mg of the protein was mixed with 6× loading buffer, followed by electrophoresis using 10% SDS-PAGE gel. The electrophoresed protein was transferred onto a polyvinylidene fluoride (PVDF) membrane by using a transfer buffer at 4° C. with 120 V for 1.5 hours. The PVDF membrane on which the protein was transferred was pretreated with a blocking buffer prepared by mixing 5% skim milk with TBS buffer (TBS-T, pH 7.6) supplemented with Tween 20 for 30 minutes, and the membrane was washed with TBS-T. The washed membrane was added with the antibody against Akt (Cell Signaling Technology, USA), Akt(T308) (Cell Signaling Technology, USA), Akt(S473) (Cell Signaling Technology, USA), FOXO3A (Cell Signaling Technology, USA), FOXO3A(S253) (Cell Signaling Technology, USA), GSK-3β (Cell Signaling Technology, USA) or GSK-3β(S9) (Cell Signaling Technology, USA) protein as a primary antibody, followed by reaction at 4° C. for 12 hours. At this time, the antibody against actin (Santa Cruz Biotechnology, USA) protein was used for the control group. Upon completion of the reaction, the secondary antibody corresponding to the primary antibody was added thereto, followed by reaction at room temperature for 30 minutes. The PVDF membrane was washed with TBS-T buffer three times. The washed PVDF membrane was added with ECL solution (Thermo Scientific, USA), followed by image observation. Images were photographed by using LAS 4000 imaging system (GE Healthcare, USA), which are shown in FIG. 1C.

As shown in FIG. 1C, the Akt protein phosphorylation and the phosphorylations of the proteins in FOXO3A and GSK-3β signaling pathways located downstream of the Akt protein phosphorylation pathway were reduced in liver cells of the high fat diet group mice (FIG. 1C).

EXAMPLE 3

Confirmation of Increased Calcium Levels in Insulin Resistance Induced Cells The following experiment was performed to investigate whether or not the intracellular calcium level was increased in the fatty liver cell model constructed in vitro by inducing insulin resistance using saturated free fatty acid (FFA).

First, human HepG2 cells were cultured in DMEM (Dulbecco's Modified Eagle Medium) supplemented with 10% fetal bovine serum (FBS), 25 mM glucose, 2 mM L-glutamine, 100 U/Ml of penicillin and 100 µg/Ml of streptomycin. At this time, the culture was performed in a 37° C., 5% $CO_2$ incubator. The cultured cells were distributed in a culture plate at the density of $5.0 \times 10^5$ cells/well, followed by further culture for overnight. Palmitic acid (PA) was added to the plate at the concentration of 0, 100, 300 or 500 µM, followed by reaction for 24 hours. Then, the concentration of calcium was investigated by using Fluo-3 AM according to the same conditions and procedures as described in Example 1, and the results are shown in FIG. 2A and FIG. 2B.

As shown in FIG. 2A and FIG. 2B, the concentration of calcium was increased in the cytoplasm of the HepG2 cells treated with PA (FIG. 2A and FIG. 2B).

EXAMPLE 4

Inhibition of Insulin Signaling Mechanism in Insulin Resistance Induced Cells To investigate the changes in insulin sensitivity when insulin was added to the fatty liver cell model constructed in vitro, the phosphorylations of those proteins that were involved in insulin signal transduction were examined. PA was added to the human HepG2 cells prepared in Example 3, followed by reaction for 24 hours. The experiment was performed by the same manner under the same conditions as described in Example 2 except that 100 nM insulin was added thereto 15 minutes before the reaction was completed.

As a result, as shown in FIG. 2C, the Akt protein phosphorylation was significantly inhibited in the PA treated cells, compared with the cells treated with insulin alone, indicating the insulin sensitivity was impaired (FIG. 2C).

EXAMPLE 5

Confirmation of Intracellular Calcium Dynamics in Insulin Resistance Induced Cells Intracellular calcium dynamics was confirmed in the fatty liver cell model constructed in vitro by inducing insulin resistance. At this time, the experiment was performed by the same manner under the same conditions as described in Example 3 except that Fura-2 AM was used instead of Fluo-3 AM.

As a result, as shown in FIG. 3, the intracellular calcium concentration was significantly increased by PA (FIG. 3).

EXAMPLE 6

Inhibition of Insulin Signaling by Changes of Intracellular Calcium Concentration <6-1> Effect of Increase of Calcium The effect of PMA (phorbol myristate acetate) and ionomycin, the drugs accelerating calcium flux, on insulin sensitivity was investigated. PMA and ionomycin are known to increase intracellular calcium and transmit a strong calcium signal.

For the experiment, human HepG2 cells were treated with PMA at the concentration of 0, 10, 50 or 100 nM instead of PA or with ionomycin at the different concentration of 0, 1, 5, 10 or 20 µM. 100 nM insulin was added thereto 15 minutes before the reaction was completed. The experiment was performed by the same manner under the same conditions as described in Example 2 except that the antibody against pAkt (T308), pAkt (S473), Akt or actin was used as the primary antibody.

As a result, as shown in FIG. 4A and FIG. 4B, the phosphorylation of Akt protein was significantly inhibited by PMA or ionomycin and at this time the inhibition was dose-dependent (FIG. 4A and FIG. 4B). Therefore, it was confirmed that the insulin sensitivity was impaired by the increase of calcium.

<6-2> Effect of Decrease of Calcium

To investigate the effect of decrease of calcium on insulin sensitivity, the following experiment was performed using verapamil, the L-type calcium channel blocker. The experiment was performed by the same manner under the same conditions as described in Example <6-1> except that verapamil was added at the concentration of 0, 5, 10 or 100 nM instead of PMA or ionomycin and the effect of insulin addition was investigated.

As a result, as shown in FIG. 4C and FIG. 4D, the phosphorylation of Akt protein was increased by verapamil (FIG. 4C and FIG. 4D), indicating that the insulin sensitivity was increased by the decrease of intracellular calcium.

Therefore, it was confirmed that the changes of intracellular calcium concentration was related to the phosphorylation of Akt protein.

EXAMPLE 7

Inhibition of Binding of Akt Protein to PI(3,4)P$_2$ or PI(3,4,5)P$_3$ by Calcium For the activation of Akt protein, Thr308 and Ser473 of Akt protein need to be phosphorylated first and then the PH domain of Akt protein has to bind to PI(3,4,5)P$_3$, and then the complex must move to the cell membrane. Thus, the present inventors investigated the effect of calcium on the binding of Akt protein to PI(3,4)P$_2$ or PI(3,4,5)P$_3$ by the following method.

<7-1> Purification of PH Domain of Akt Protein

First, PCR was performed to obtain the PH domain of Akt1 protein (SEQ. ID. NO: 13) by using the primers consisting of the nucleotide sequences represented respectively by SEQ. ID. NO: 3 and SEQ. ID. NO: 4 as listed in Table 1 below. The obtained PCR product was cloned in pET28a vector (Novagen, USA).

TABLE 1

| Name | Sequence (5'→3') | SEQ. ID. NO: |
|---|---|---|
| hPKCβ1_C2_PN127 (NcoI) | AAACCATGGGCCACCAGGGGATGAAATGTGACACC | SEQ. ID. NO: 1 |
| hPKCβ1_C2_PC296 (XhoI) | AAACTCGAGCAGATCCTCTTCTGAGATGAGTTTTTGTTCCTCACTTCCTTCTGGTGGCACAGG | SEQ. ID. NO: 2 |
| hAkt1_PH_PN1 (SacI) | AAAGAGCTCATGGGCAGCGACGTGGCTAT | SEQ. ID. NO: 3 |
| hAKT1_PH_PC144 (SpeI) | AAAACTAGTTCAGTGGTGGTGGTGGTGGTGGCGGTGCTTGGGCTTGGCCA | SEQ. ID. NO: 4 |
| hPKCβ1_C2_PN159 (BglII) | AAAAGATCTATGCGCGGCCGCATCTACATCCA | SEQ. ID. NO: 5 |
| hPKCβ1_C2_PC289 (BanHI) | AAAGGATCCAGGCACATTGAAGTACTCGC | SEQ. ID. NO: 6 |
| hAkt1_PH_PN6 (BglII) | AAAAGATCTATGATTGTGAAGGAGGGTTGG | SEQ. ID. NO: 7 |
| hAkt1_PH_PN111 (BamHI) | AAAGGATCCCTTGAGGCCGTCAGCCAC | SEQ. ID. NO: 8 |
| hPKCβ1_C2_PN127 (BglII) | AAAAGATCTCGCTCATTGTCCTCGTAAGAGA | SEQ. ID. NO: 9 |
| hPKCβ1_C2_PC296 (NheI) | AAAGCTAGCGGACAAAGATCCCATGAAGT | SEQ. ID. NO: 10 |
| hAKT1_kinase_PN (NheI) | AAAGCTAGCTTTGAGTACCTGAAGCTGCT | SEQ. ID. NO: 11 |
| hAKT1_kinase_PC (KpnI) | AAAGGTACCTCAGGCCGTGCCGCTGGCCG | SEQ. ID. NO: 12 |

*E. coli* BL21 (DE3) cells were transfected with a vector containing the PH domain of Akt protein, and the cells were cultured in 50 Ml of LB medium supplemented with 50 μg/Ml of kanamycin. The culture was performed at 37° C. for 8 hours. Upon completion of the culture, the cells were transferred into a 25° C. agitation incubator. The cells were cultured until $OD_{600}$ reached 0.6 to 1.0, and then 1 mM IPTG (isopropyl-β-D-1-thiogalactopyranoside) was added thereto. 18 hours after the addition of IPTG, centrifugation was performed at 7,000×g at 4° C. for 10 minutes to to obtain cells. Sonication equilibrium buffer (150 mM NaCl, 50 mM Tris-HCl, pH 7.6) was added to the obtained cells. The cells added with the sonication equilibrium buffer were lysed by sonication. The PH domain of Akt protein was purified from the cell lysate by gel filtration chromatography using nickel-nitrilotriacetic acid and HiLoad Superdex-200 column (GE Healthcare life science, USA). The purity of the purified protein was examined by SDS-PAGE (sodium dodecyl sulfate polyacrylamide gel electrophoresis).

<7-2> Inhibition of Binding of Akt Protein PH Domain to $PI(3,4)P_2$ or $PI(3,4,5)P_3$ by Calcium-1

The effect of calcium on the binding of the PH domain of Akt protein to $PI(4,5)P_2$ or $PI(3,4,5)P_3$ was investigated by protein-lipid binding assay.

Particularly, the analysis was performed by using membrane-immobilized lipid strips (PIP-strips, Echelon Biosciences Inc., USA). At this time, the membrane was loaded with LPA (lysophosphatidic acid), LPC (lysophosphatidylcholine), PI (phosphatidylinositol), PE (phosphatidylethanolamine), PC (phosphatidylcholine), S1P (sphingosine 1-phosphate), PA (phosphatidic acid) or PS (phosphatidylserine) at the concentration of 100 pmol, to which calcium was added at the concentration of 0, 0.05 or 0.1 mM. Each membrane was pre-treated with a blocking buffer [fatty acid free 3% BSA (bovine serum albumin), 0.1% (v/v) Tween 20 and TBS (Tris-buffered saline), pH 7.5] at room temperature for 30 minutes. The PH domain of Akt protein purified in Example <7-1> was suspended in a blocking buffer at the concentration of 3.5 mg/Ml. The suspended protein was reacted with the membrane-immobilized lipid strip at room temperature for 30 minutes. The protein bound with lipid was identified by using the PH domain antibody.

As a result, as shown in FIG. 5, the PH domain of Akt protein was bound to $PI(3,4)P_2$ or $PI(3,4,5)P_3$ and the binding was inhibited as calcium concentration was increased (FIG. 5).

<7-3> Inhibition of Binding of Akt Protein PH Domain to $PI(3,4)P_2$, $PI(4,5)P_2$ or $PI(3,4,5)P_3$ by Calcium-2

The effect of calcium on the binding of the PH domain of Akt protein to $PI(3,4)P_2$, $PI(4,5)P_2$ or $PI(3,4,5)P_3$ was investigated by ITC (isothermal titration calorimetry).

Particularly, a protein solution was prepared by suspending a protein in 10 mM HEPES (pH 7.0). Phospholipid related ligand was titrated in the protein solution at 25° C. by using iTC200 micro calorimetry system (MicroCal Inc., USA), and the generated graph was corrected using Origin software (MicroCal Inc., USA). At this time, the phospholipid related ligand was prepared in the form of liposome by mixing POPC (1-palmitoyl-2-oleoyl-sn-glycero-3-phosphocholin) chloroform solution and POPS (1-palmitoyl-2-oleoyl-sn-glycero-3-phosphoserine), $PI(3,4)P_2$ (1,2-dipalmotoyl-sn-glycero-3-phosphatidylinositol-3,4- triphosphate), PI(4,5)P$_2$ (1,2-dipalmotoyl-sn-glycero-3-phosphatidylinositol-4,5-trisphosphate) or PI(3,4,5)P$_3$ (1,2-dipalmotoyl-sn-glycero-3-phosphatidylinositol-3,4,5-trisphosphate) at the molar ratio of 80:20. The organic solvent was eliminated. The organic solvent was removed and a single layer lamellar was produced in HEPES (pH 7.0) using phospholipids.

As a result, as shown in FIG. 6A to FIG. 6C, PI(3,4)P$_2$, PI(4,5)P$_2$ or PI(3,4,5)P$_3$ was bound to calcium with a high affinity, unlike POPS (FIG. 6A~FIG. 6D). In particular, PI(3,4,5)P$_3$ had two calcium binding sites (FIG. 6E), so the binding force was further increased.

From the above results, it was confirmed that PI(3,4,5)P$_3$, PI(3,4)P$_2$ and PI(4,5)P$_2$ had a strong binding force to calcium and once intracellular calcium was accumulated, the binding force of the Akt protein PH domain thereto was reduced. In a healthy condition, the phosphate group in the carbon ring of PI(3,4,5)P$_3$ has negative charge and the PH domain has positive charge, so that they are bound together stably. In the obese state, the intracellular calcium concentration is increased, so that calcium is bound to the phosphate group of PI(3,4,5)P$_3$. Thus, the interaction between PI(3,4,5)P$_3$ and the PH domain does not occur (FIG. 7).

EXAMPLE 8

Confirmation of Binding of PKCβ Protein C2 Domain to PI(4,5)P$_2$ or PI(3,4,5)P$_3$ It was investigated whether or not the C2 domain having the characteristic of interacting with calcium like the PH domain of Akt protein was bound to PI(4,5)P$_2$ or PI(3,4,5)P$_3$. The C2 domain above is found in approximately 362 kinds of proteins in human and total 582 C2 domains are known to exist. Particularly, the C2 domain is found in PLC, PI3K and PKC proteins. The C2 domain either has a calcium binding site for direct binding to calcium or can bind to PIP calcium independently.

<8-1> Purification of C2 Domain of PKCβ Protein

The C2 domain of PKCβ protein (SEQ. ID. NO: 14) was purified by the same manner under the same conditions as described in Example <7-1> except that the primers consisting of the nucleotide sequences represented by SEQ. ID. NO: 1 and SEQ. ID. NO: 2 listed in Table 1 were used. In the meantime, D187/193A and D246/248A, the C2 domain mutant forms, were purified as for the control by the same manner.

<8-2> Inhibition of Binding of PKCβ Protein C2 Domain to PI(4,5)P$_2$ or PI(3,4,5)P$_3$ by Calcium To investigate whether or not the binding of the PKCβ protein C2 domain purified in Example <8-1> to PI(4,5)P$_2$ or PI(3,4,5)P$_3$ was inhibited by calcium, protein lipid binding assay and ITC were performed. First, protein-lipid binding assay was performed by the same manner under the same conditions as described in Example <7-2> except that the PKCβ protein C2 domain was used instead of the Akt protein PH domain. At this time, D187/193A and D246/248A mutant proteins of the C2 domain were used as the control group, and the results are shown in FIG. 8.

As shown in FIG. 8, the C2 domain of PKCβ protein was strongly bound to PI(4,5)P$_2$ and PI(3,4,5)P$_3$ (FIG. 8).

In the meantime, in ITC, the phospholipid related ligand was prepared in the form of liposome by mixing POPC chloroform solution and PI(3,4,5)P$_3$ at the molar ratio of 80:20. Then, ITC was performed by the same manner under the same conditions as described in Example <7-3> except that the PKCβ protein C2 domain or D187/193A, the C2 domain mutant, was used. The results are shown in FIG. 9.

As shown in FIG. 9B, the PKCβ protein C2 domain was strongly bound to PI(3,4,5)P$_3$ (FIG. 9B). However, the C2 domain mutant form D187/193A which had a mutation on the calcium binding site of the C2 domain was barely bound to PI(3,4,5)P$_3$ (FIG. 9C). Therefore, it was confirmed that D187 residue and D193 residue in the C2 domain were the ones that directly interacted with calcium.

EXAMPLE 9

Migration of PH or C2 Domain According to Calcium Concentration

From the above results, it was confirmed that the PH domain of Akt protein or the C2 domain of PKCβ protein was bound to the cell membrane. Thus, the present inventors performed immunostaining to investigate the effect of calcium concentration change on the binding of such domains above to the cell membrane.

First, the PH domain of Akt1 protein or C2 domain of PKCβ protein was obtained by PCR using the primers consisting of the nucleotide sequences represented by SEQ. ID. NO: 5~SEQ. ID. NO: 8 listed in Table 1 above. The obtained PCR product was cloned in pmCherry-C1 vector (Takara Clontech, Japan) by the conventional cloning method. CHO cells were transfected with the prepared vector by using lipofectamine according to the manufacturer's protocol. The transfected cells were selected by using blastidicin. Then, mCherry positive cells were confirmed by flow cytometry.

PMA at the concentration of 100 nM, ionomycin at the concentration of 10 μM or insulin at the concentration of 100 nM was added to the cells expressing the PH domain of Akt1 protein or the C2 domain of PKCβ protein and the location of the expressed protein was confirmed by fluorescence microscopy. The results are shown in FIG. 10.

As shown in FIG. 10A, the PH domain ted to the cell membrane by the addition of insulin. When the intracellular calcium concentration was increased, the migration to the cell membrane was not observed (FIG. 10A). However as shown in FIG. 10B, the C2 domain did not migrate to the cell membrane even when insulin was added, but migrated as the intracellular calcium concentration was increased (FIG. 10B).

From the above results, it was confirmed that when the calcium concentration was increased, the binding of the PH domain of Akt protein to PI(3,4,5)P$_3$ was inhibited but the binding of the C2 domain to PI(3,4,5)P$_3$ was not affected even under the condition of increased calcium because the C2 domain was interacted with the up-regulated calcium as well.

EXAMPLE 10

Effect of PKCβ Protein C2 Domain and Akt Protein Fusion Protein on Akt Activation A fusion protein was prepared by using the C2 domain of PKCβ protein instead of the PH domain of Akt protein. It was investigated that the Akt activation was dependent on PI3K under the condition of increased calcium concentration induced by the fusion protein.

First, the C2 domain of PKCβ protein and Akt protein (SEQ. ID. NO: 15) were obtained by PCR using the primers consisting of the nucleotide sequences represented by SEQ.

ID. NO: 9~SEQ. ID. NO: 12 listed in Table 1 above. The obtained PCR product was cloned in pEGFP-C2 vector by the conventional cloning method, resulting in the construction of a vector expressing the C2 domain/Akt protein fusion protein (SEQ. ID. NO: 17) (C2-Akt fusion protein). At this time, as the control group, a vector expressing the wild type Akt protein containing the PH domain was prepared.

HepG2 cells were transfected with the vector expressing the C2-Akt fusion protein constructed above along with the vector expressing PI3K protein by using lipofectamine according to the manufacturer's protocol. The transfected cells were treated with PMA at the concentration of 0, 10, 50 or 100 nM ionomycin at the concentration of 20 µM, followed by reaction for 1 hour. Western blot analysis was performed with the cells above. The experiment was performed by the same manner under the same conditions as described in Example 2 except that the antibody against Akt (Cell Signaling Technology, USA), Akt(T308) (Cell Signaling Technology, USA), Akt(S473) (Cell Signaling Technology, USA), FOXO3A (Cell Signaling Technology, USA), FOXO3A(S253) (Cell Signaling Technology, USA), GSK-3β (Cell Signaling Technology, USA), GSK-3β(S9) (Cell Signaling Technology, USA) or PI3K (Cell Signaling Technology, USA) protein was used as the primary antibody.

As a result, as shown in FIG. 11 and FIG. 12, Akt protein was activated by PI3K in the cells transfected with the wild type Akt protein and the activation was inhibited as the calcium concentration increased. However, the Akt protein activation was not inhibited but increased by the increase of calcium concentration in the cells transfected with the C2-Akt fusion protein (FIG. 11 and FIG. 12).

EXAMPLE 11

Confirmation of Signal Transduction Mechanism by PKCβ Protein C2 Domain and Akt Protein Fusion Protein The following experiment was performed to investigate which of PI(4,5)P$_2$ and PI(3,4,5)P$_3$P1 was more important for the activation of Akt protein by the C2-Akt fusion protein.

Particularly, the experiment was performed by the same manner under the same conditions as described in Example 2 except that the vector expressing the C2-Akt fusion protein and the vector expressing PI3K protein were co-treated with PTEN or SHIP2 and the antibody against Akt (Cell Signaling Technology, USA), Akt(T308) (Cell Signaling Technology, USA), Akt(S473) (Cell Signaling Technology, USA), PI3K (Cell Signaling Technology, USA), PTEN (Cell Signaling Technology, USA) or SHIP2 (Upstate Biotechnology, USA) protein was used as the primary antibody.

As a result, as shown in FIG. 13, the Akt protein activity was reduced by the increase of intracellular PI(4,5)P$_2$ induced by PTEN or SHIP2 (FIG. 13). So, it was confirmed that PI(3,4,5)P$_3$ was more important than PI(4,5)P$_2$ in changing the Akt protein activation by the C2-Akt fusion protein.

EXAMPLE 12

Confirmation of C2 Domain/Calcium Binding Site in PKCβ Protein C2 Domain and Akt Protein Fusion Protein From the above results, it was confirmed that the C2-Akt fusion protein was able to activate Akt by binding to PIP conjugated calcium even under the condition of high calcium concentration. Therefore, the following experiment was performed to investigate which residue among the calcium binding residues existing in the C2 domain played the most important role.

First, a mutant form of the C2-Akt fusion protein was constructed by mutating a residue known as a calcium binding site in the C2-Akt fusion protein C2 domain. Particularly, D187/193A, D246/248A or D254T mutant from of the C2 domain was constructed (FIG. 14A). HepG2 cells were transfected with the vector expressing PI3K protein together with the C2-Akt fusion protein mutant form by using lipofectamine according to the manufacturer's protocol. The transfected cells were treated with ionomycin at the concentration of 10 µM, followed by reaction for 1 hour. Western blot analysis was performed with the cells above. The experiment was performed by the same manner under the same conditions as described in Example 2 except that the antibody against Akt (Cell Signaling Technology, USA), Akt(T308) (Cell Signaling Technology, USA), Akt(S473) (Cell Signaling Technology, USA) or PI3K (Cell Signaling Technology, USA) protein was used as the primary antibody.

As a result, as shown in FIG. 14B and FIG. 14C, the D246/248A or D254 mutant fusion protein was still able to activate Akt protein in the presence of PI3K, but the D187/193A mutant did not activate Akt protein. From the above results, it was confirmed that the D187 and D193 residues of the C2 domain were important for the C2-Akt fusion protein to activate Akt protein under the condition of high calcium concentration.

EXAMPLE 13

Treatment Effect of PKCβ Protein C2 Domain and Akt Protein Fusion Protein on Obesity Induced Insulin Resistance <13-1> Confirmation of Infection with Adenovirus Expressing PKCβ Protein C2 Domain and Akt Protein Fusion Protein and Weight Changes of Animal Model Infected with Adenovirus Thereof The treatment effect of the C2-Akt fusion protein on insulin resistance in the insulin resistance animal model induced by high fat diet mediated obesity was investigated as follows.

First, male C57BL/6 mice at 8 weeks were fed with HFD diet (60% high fat diet) for 8 weeks to construct an obesity-induced insulin resistance animal model.

In the meantime, Ad-Akt and Ad-C2Akt expression vectors were prepared by cloning the wild type Akt protein or the C2-Akt fusion protein into adenovirus vector (FIG. 15A). At this time, Ad-GFP, the expression vector expressing GFP, was constructed as a control. AD-293 cells (Invitrogen, USA) were infected with the constructed vector above by the conventional method well known to those in the art, and the virus was amplified. The amplified viruses were purified by using ViraBind-Adenovirus Purification Kit (Cell Biolabs Inc., USA) according to the manufacturer's protocol. The purified virus was titrated. The constructed mouse model was administered with the virus at the dose of $1 \times 10^9$ PFU through intravenous injection. The mouse injected with the virus was observed for 2 weeks, followed by autopsy (FIG. 15B).

For 2 weeks after the virus injection, the weight change and the feed intake of the mouse were observed and the results are shown in FIG. 16. The fat amount and the changes of dry weight were observed and the results are shown in FIG. 17. As shown in FIG. 16, the body weight of the mouse infected with the adenovirus vector expressing the C2-Akt fusion protein was reduced (FIG. 16A), but the feed intake was not much different from that of the control mouse (FIG. 16B). As shown in FIG. 17, the fat amount and the dry weight of the mouse infected with the adenovirus vector expressing the C2-Akt fusion protein were reduced, compared with the control (FIG. 17).

Therefore, it was confirmed that obesity in the insulin resistance animal model induced by high fat diet mediated obesity was improved by the C2-Akt fusion protein.

<13-2> Confirmation of Glucose Tolerance and Insulin Resistance According to PKCβ Protein C2 Domain and Akt Protein Fusion Protein Glucose tolerance and insulin resistance in the mouse infected with the adenovirus vector expressing the C2-Akt fusion protein prepared in Example <13-1> were examined by the following method.

Particularly, the adenovirus vector was injected in the mouse and then the mouse was fasted for 16 hours. The fasted mouse was intraperitoneally injected with glucose (Fisher Scientific, USA) at the concentration of 1 g per 1 kg of the mouse weight (Fisher Scientific, USA). Blood was collected from the tail vein of the mouse model injected with glucose, and the glucose level in the blood sample was measured using a glucose monitor. The results are shown in FIG. 18A and FIG. 18B.

In the meantime, the adenovirus vector was injected into the mouse model and the mouse was fasted for 4 hours. The fasted mouse was intraperitoneally injected with insulin at the concentration of 0.65 unit per 1 kg of the mouse weight. The blood sample was allowed to settle on ice for 1 to 2 hours to coagulate. The coagulated blood was centrifuged at 8,000 rpm at 4° C. for 10 minutes, and only serum was obtained. The insulin level in the obtained serum was measured by using an ELISA kit (Millipore, USA) according to the manufacturer's protocol. The results are shown in FIG. 18C and FIG. 18D.

As shown in FIG. 18A and FIG. 18B, the glucose level in the mouse infected with the adenovirus vector expressing the C2-Akt fusion protein was lower than that of the control (FIG. 18A and FIG. 18B) but the insulin level was not significantly different (FIG. 18C and FIG. 18D).

<13-3> Confirmation of HOMA-IR Changes According to PKCβ Protein C2 Domain and Akt Protein Fusion Protein To examine the glucose tolerance and insulin resistance in Example <13-2> blood samples were taken from the fasting animal model before injection of glucose or insulin to determine fasting glucose or insulin levels. HOMA-IR (homeostatic model assessment of insulin resistance) values were calculated from the glucose and insulin levels obtained above. The experiment was performed by the same manner under the same conditions as described in Example <13-2> except that the blood sample was obtained from the fasting mouse. HOMA-IR values were calculated by the mathematical formula 1 below with the measured glucose and insulin levels.

HOMA-IR=fasting blood glucose (mg/dl)×fasting insulin (μU/Ml)/22.5    [Mathematical Formula 1]

As a result, as shown in FIG. 19, it was confirmed that the fasting glucose and insulin levels were reduced by the C2-Akt fusion protein. It was also confirmed from the HOMA-IR results that the insulin resistance was improved by the C2-Akt fusion protein (FIG. 19).

<13-4> Confirmation of Changes in Blood Component According to PKCβ Protein C2 Domain and Akt Protein Fusion Protein Blood samples were collected from the mouse injected with the adenovirus vector expressing the C2-Akt fusion protein in Example <13-1>, from which the levels of ALT (alanine aminotransferase), total cholesterol and LDL (low density lipoprotein) were measured.

Particularly, the obtained blood sample was centrifuged at 3,000 rpm at 4° C. for 15 minutes, and only serum was obtained. The levels of ALT, total cholesterol and LDL in the obtained serum were measured by using an AU480 chemical analyzer (Beckman Coulter, USA) and the results are shown in FIG. 20.

As shown in FIG. 20, the levels of ALT, total cholesterol and LDL were all reduced in the mouse infected with the adenovirus vector expressing the C2-Akt fusion protein (FIG. 20). Therefore, it was confirmed that the C2-Akt fusion protein was able to improve the liver function of the insulin resistance animal model induced by high fat diet mediated obesity.

<13-5> Confirmation of Reduction of Liver Lipid Droplets According to PKCβ Protein C2 Domain and Akt Protein Fusion Protein Liver tissues were extracted from the mouse infected with the adenovirus vector expressing the C2-Akt fusion protein prepared in Example <13-1>, followed by H&E staining to confirm the reduction of liver lipid droplets.

Particularly, the liver was extracted from the mouse (FIG. 21A), which was then fixed in 10% (v/v) neutral formalin buffer. One week later, the liver was sliced to obtain the sections with a thickness of 5 μm, which were embedded in paraffin. The embedded tissue was loaded in xylene to eliminate wax, followed by rehydration with alcohol solution. The rehydrated liver tissue sections were mounted on the slide glass, followed by H&E (hematoxylin & eosin) staining. Then, lipid droplets were observed under microscope and the results are shown in FIG. 21B.

As shown in FIG. 21B, the lipid droplets were significantly reduced in the mouse infected with the adenovirus vector expressing the C2-Akt fusion protein, unlike the control mouse (FIG. 21B). From the above results, it was confirmed that the C2-Akt fusion protein had the effect of improving the fatty liver induced by high fat diet by inducing the normal Akt signal transduction.

<13-6> Insulin Signaling Mechanism in Liver According to PKCβ Protein C2 Domain and Akt Protein Fusion Protein The Insulin signaling mechanism was investigated by the same manner under the same conditions as described in Example 2 except that the liver tissues obtained from the mouse infected with the adenovirus vector expressing the C2-Akt fusion protein prepared in Example <13-1> were used.

As a result, as shown in FIG. 22, the phosphorylation levels of Akt, GSK3β and FOXO3A were increased in the mouse infected with the adenovirus vector expressing the C2-Akt fusion protein. Therefore, it was confirmed that the C2-Akt fusion protein activated Akt and thus moved the C2-Akt fusion protein to the membrane even in the high fat diet mouse model displaying a higher intracellular calcium concentration.

<13-7> Confirmation of Expression Patterns of Fatty Liver Related Genes According to PKCβ Protein C2 Domain and Akt Protein Fusion Protein Real time PCR was performed with the liver tissues obtained from the mouse infected with the adenovirus vector expressing the C2-Akt fusion protein obtained in Example <13-1> in order to investigate the expression patterns of the genes involved in glucose synthesis, fat synthesis or fat absorption.

Particularly, 1 Ml of trizol (Invitrogen, USA) was added to 13 mg of the liver tissues obtained in Example <13-1>. The liver tissues treated with trizol were lysed by using a tissue homogenizer, to which 200 μl of chloroform was added. The lysate was centrifuged at 12,000 rpm for 20 minutes to obtain a supernatant. 500 μl of isopropanol was added to the obtained supernatant, followed by vortexing. The reaction mixture stood at room temperature for 10 minutes, and then proceeded to centrifugation at 12,000 rpm for 15 minutes to obtain a pellet. The obtained pellet was washed with ethanol, and then dried at room temperature. The pellet was suspended in distilled water treated with 40 μl of DEPC (diethylpyrocarbonate), from which RNA was isolated. The isolated RNA was quantified by using a nano-drop UV-his spectrophotometer (Thermo Scientific, USA) and then stored at −80° C. until use.

From the isolated RNA, cDNA was synthesized using a cDNA synthesis kit (Takara Bio, Japan) according to the manufacturer's protocol. Particularly, a proper amount of DNaseI was added to 4 μg of RNA, followed by reaction at 37° C. for 30 minutes and another further reaction at 75° C. for 10 minutes. Upon completion of the reaction, 1 μl of random hexamer primer, 1 μl of dNTP mixture and 3 μl of sterilized distilled water were added to 5 μl of the reaction solution above, followed by further reaction at 65° C. for 5 minutes. 4 μl of 5× PrimeScript buffer, 0.5 μl of RNase inhibitor, 1 μl of RNase and 4.5 μl of sterilized distilled water were added to the reaction solution above, followed by reaction at 30° C. for 10 minutes, at 42° C. for 40 minutes and at 72° C. for 10 minutes. Upon completion of the reaction, 80 μl of sterilized distilled water was added thereto and the synthesized cDNA was stored at −20° C. until use.

Real-time PCR was performed using the synthesized cDNA. Particularly, qRT-PCR (quantitative real-time PCR) was performed by using CFX384 real-time PCR detection system (Bio-Rad, USA) with the cycle of reaction at 95° C. for 10 minutes, at 95° C. for 15 minutes (40 times) and 60° C. for 1 minute. At this time, the primers known to be capable of detecting G6PC, PEPCK, SREBP1C, FAS, AccI, Acc2, ChREBP, Mttp, CD36, Ldlr and CPT1 genes were used as the primers for detecting each gene. The relative expression levels of the gene products obtained by qRT-PCR were normalized on the basis of the expression level of cyclophilin gene and calculated by ΔΔCt method.

As a result, as shown in FIG. 23A to FIG. 23C, the expressions of G6PC, PEPCK, SREBP1C, FAS, Acc1, Acc2, ChREBP, Mttp, CD36, Ldlr and CPT1, the genes involved in glucose synthesis, fat synthesis and fat absorption, were reduced in the mouse infected with the adenovirus vector expressing the C2-Akt fusion protein (FIG. 23A~FIG. 23C).

<13-8> Confirmation of Expression Patterns of Fatty Liver Related Proteins According to PKCβ Protein C2 Domain and Akt Protein Fusion Protein Western blotting was performed to investigate whether or not the inhibition of those genes involved in glucose synthesis, fat synthesis or fat absorption in the liver of the mouse treated with high fat diet induced by the C2-Akt fusion protein affected on the protein expression.

The experiment was performed by the same manner under the same conditions as described in Example 2 except that the liver tissues obtained from the mouse infected with the adenovirus vector expressing the C2-Akt fusion protein were used and the antibodies against pSREBP-1 (Santa Cruz Biotechnology, USA), nSREBP-1 (Santa Cruz Biotechnology, USA), FAS (Santa Cruz Biotechnology, USA), ACC1 (Santa Cruz Biotechnology, USA) and ACC2 (Santa Cruz Biotechnology, USA) proteins were used as the primary antibodies.

As a result, as shown in FIG. 23D, the expressions of ACC1 and ACC2 proteins were reduced in the mouse infected with the adenovirus vector expressing the C2-Akt fusion protein (FIG. 23D).

EXAMPLE 14

Confirmation of Gene Expression Changes According to PKCβ Protein C2 Domain and Akt Protein Fusion Protein The expression changes of RNA expressed in the liver of the mouse infected with the adenovirus vector expressing the C2-Akt fusion protein prepared in Example <13-1> were investigated by RNA sequencing. As a result, as shown in FIG. 24A, 5 genes that were up-regulated by the C2-Akt fusion protein and 7 genes that were down-regulated by the fusion protein were confirmed.

The following experiment was performed to investigate the gene expression patterns by the same manner under the same conditions as described in Example <13-5> except that the liver tissues of the mouse and the known primers known to be capable of detecting LCN2, Selenbp, FABP5, Orm2, FGFR1, Acot3, RGS16, Lpin1, Vnn1, K1f10, Cidea, Cideb or CideC genes were used.

As a result, as shown in FIG. 24B to FIG. 24D, the expressions of the genes playing a role in improving fatty liver such as LCN2, Selenbp2, FABP5, Orm2 and Fgfr1 were increased by the C2-Akt fusion protein, while the expressions of the genes known to accelerate fatty liver such as Acot3, Rgs16, Lpin1, Vnn1 and K1f10 were decreased (FIG. 24B and FIG. 24C). In the meantime, the expressions of the genes involved in lipid droplet production and fat accumulation such as Cidea (cell death inducing DNA fragmentation factor-alpha-like effector protein a) and Cidec were also decreased (FIG. 24D).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method of screening candidate drugs for treating a metabolic disease selected from the group consisting of obesity, insulin resistance, diabetes, and fatty liver, the method comprising the following steps:
    selecting cells of an obesity cell model, an insulin resistance cell model, a diabetes cell model, or a fatty liver cell model, the selected cells having an increased intracellular calcium concentration;
    measuring interaction between calcium and phosphatidylinositol phosphate (PIP) in the selected cells;
    applying a drug candidate to the selected cells to produce tested cells;
    measuring the interaction between calcium and phosphatidylinositol phosphate (PIP) in the tested cells; and
    selecting a drug candidate that, when applied to the selected cells, inhibits or reduces the measured interaction between calcium and PIP.

2. The method according to claim 1, wherein the PIP is phosphatidylinositol (3,4,5)-triphosphate, phosphatidylinositol (4,5)-bisphosphate or phosphatidylinositol (4,5)-bisphosphate.

3. The method according to claim 1, wherein measuring interaction between calcium and PIP is achieved by one or more methods selected from the group consisting of ITC (isothermal titration calorimetry) and protein-lipid binding assay.

4. The method according to claim 1, wherein the drug candidate, when applied to the selected cells, inhibits migration of a protein containing C2 domain to the cell membrane of the selected cells.

5. The method to claim 4, wherein the protein containing C2 domain is selected from the group consisting of PI3K (phosphatidylinositol 3-kinase), PKC(protein kinase C), ABR (active breakpoint cluster region-related), BAIAP3 (BAI1-associated protein 3), BCR (breakpoint cluster region), C2CD2 (C2 calcium dependent domain containing 2), C2CD3 (C2 calcium dependent domain containing 3), CADPS (calcium-dependent secretion activator 1), CADPS2 (calcium-dependent secretion activator 2), CAPN5 (calpain-5), CAPN6 (calpain-6), CC2D1A (coiled-coil and C2 domain-containing protein 1A), CC2D1B (coiled-coil and C2 domain-containing protein 1B), CPNE1 (copine-1), CPNE2 (copine-2), CPNE3 (copine-3), CPNE4 (copine-4), CPNE5 (copine-5), CPNE6 (copine-6), CPNE7 (copine-7), CPNE8 (copine-8), CPNE9 (copine-9), DAB2IP (disabled homolog 2-interacting protein), DOC2A (double C2-like domain-containing protein alpha), DOC2B (double C2-like domain-containing protein beta), DYSF (dysferlin), ESYT1 (extended synaptotagmin-1), ESYT3 (extended synaptotagmin-3), FAM62B (extended synaptotagmin-2), FER1L3 (myoferlin), FER1L5 (fer-1 like family member 5), HECW1 (C2 and WW domain containing E3 ubiquitin protein ligase 1), HECW2 (C2 and WW domain containing E3 ubiquitin protein ligase 1), ITCH (itchy E3 ubiquitin protein ligase), ITSN1 (intersectin-1), ITSN2 (intersectin-2), MCTP1 (multiple C2 and transmembrane domain containing 1), MCTP2 (multiple C2 and transmembrane domain containing 2), MTAC2D1 (tandem C2 domains nuclear protein), NEDD4 (neural precursor cell expressed developmentally down-regulated protein 4), NEDD4L (neural precursor cell expressed developmentally down-regulated gene 4-like), OTOF (otoferlin), PCLO (protein piccolo), PIK3C2A (phosphatidylinositol-4-phosphate 3-kinase C2 domain-containing alpha), PIK3 C2B (phosphatidylinositol-4-phosphate 3-kinase C2 domain-containing beta), PIK3 C2G (phosphatidylinositol-4-phosphate 3-kinase C2 domain-containing gamma), PLA2G4A (cytosolic phospholipase A2), PLA2G4B (cytosolic phospholipase A2 beta), PLA2G4D (cytosolic phospholipase A2 delta), PLA2G4E (cytosolic phospholipase A2 epsilon), PLA2G4F (cytosolic phospholipase A2 zeta), PLCB 1 (1-phosphatidylinositol-4,5-bisphosphate phosphodiesterase beta-1), PLCB 2 (1-phosphatidylinositol-4,5-bisphosphate phosphodiesterase beta-2), PLCB 3 (1-phosphatidylinositol-4,5-bisphosphate phosphodiesterase beta-3), PLCB 4 (1-phosphatidylinositol-4,5-bisphosphate phosphodiesterase beta-4), PLCD1 (phospholipase C delta 1), PLCD3 (phospholipase C delta 3), PLCD4 (phospholipase C delta 4), PLCE1 (phospholipase C epsilon 1), PLCG1 (phospholipase C gamma 1), PLCG2 (phospholipase C gamma 2), PLCH1 (phospholipase C eta 1), PLCH2 (phospholipase C eta 2), PLCL1 (phospholipase C like 1), PLCL2 (phospholipase C like 2), PLCZ1 (phospholipase C zeta 1), PRF1 (perforin-1), PRKCA (protein kinase C alpha), PRKCB1(protein kinase C beta type), PRKCE(protein kinase C epsilon), PRKCG (protein kinase C gamma), PRKCH (protein kinase C eta), RAB11FIP1 (Rab11 family-interacting protein 1), RAB11FIP2 (Rab11 family-interacting protein 2), RAB11FIP5 (Rab11 family-interacting protein 5), RASA1 (RAS p21 protein activator 1), RASA2 (RAS p21 protein activator 2), RASA3 (RAS p21 protein activator 3), RASA4 (RAS p21 protein activator 4), RASAL1 (RAS protein activator like 1), RASAL2 (RAS protein activator like 2), RGS3 (regulator of G-protein signaling 3), RIMS1 (regulating synaptic membrane exocytosis protein 1), RIMS2 (regulating synaptic membrane exocytosis protein 2), RIMS3 (regulating synaptic membrane exocytosis protein 3), RIMS4 (regulating synaptic membrane exocytosis protein 4), RPGRIP1 (X-linked retinitis pigmentosa GTPase regulator-interacting protein 1), RPH3A (rabphilin-3A), SMURF1 (E3 ubiquitin-protein ligase SMURF1), SMURF2 (E3 ubiquitin-protein ligase SMURF2), SYNGAP1 (synaptic Ras GTPase-activating protein 1), SYT1 (synaptotagmin-1), SYT10 (synaptotagmin-10), SYT11 (synaptotagmin-11), SYT12 (synaptotagmin-12), SYT13 (synaptotagmin-13), SYT14 (synaptotagmin-14), SYT15 (synaptotagmin-15), SYT16 (synaptotagmin-16), SYT17 (synaptotagmin-17), SYT2 (synaptotagmin-2), SYT3 (synaptotagmin-3), SYT4 (synaptotagmin-4), SYT5 (synaptotagmin-5), SYT6 (synaptotagmin-6), SYT7 (synaptotagmin-7), SYT8 (synaptotagmin-8), SYT9 (synaptotagmin-9), SYTL1 (synaptotagmin like 1), SYTL2 (synaptotagmin like 2), SYTL3 (synaptotagmin like 3), SYTL4 (synaptotagmin like 4), SYTL5 (synaptotagmin like 5), TOLLIP (toll interacting protein), UNC13A (Unc-13 homolog A), UNC13B (Unc-13 homolog B), UNC13C (Unc-13 homolog C), UNC13D (Unc-13 homolog D), WWC2 (WW and C2 domain containing 2), WWP1 (WW domain containing E3 ubiquitin protein ligase 1), WWP2 (WW domain containing E3 ubiquitin protein ligase 2), and PTEN (phosphatase and tensin homolog).

6. The method according to claim 4, wherein the C2 domain is a polypeptide consisting of the amino acid sequence represented by SEQ. ID. NO: 14.

7. The method according to claim 1, wherein the drug candidate, when applied to the selected cells, promotes or enhances migration of Akt protein containing PH domain to the cell membrane.

8. The method according to claim 7, wherein the Akt protein is a polypeptide consisting of the amino acid sequence represented by SEQ. ID. NO: 16.

9. The method according to claim 1, wherein the selected drug candidate, when applied to the selected cells,
    inhibits migration of a protein containing C2 domain to the cell membrane of the selected cells, and
    promotes or enhances migration of Akt protein containing PH domain to the cell membrane of the selected cells.

10. The method according to claim 9, wherein the C2 domain is a polypeptide consisting of the amino acid sequence represented by SEQ. ID. NO: 14.

11. The method according to claim 9, wherein the Akt protein is a polypeptide consisting of the amino acid sequence represented by SEQ. ID. NO: 16.

12. The method to claim 9, wherein the protein containing C2 domain is selected from the group consisting of PI3K (phosphatidylinositol 3-kinase), PKC(protein kinase C), ABR (active breakpoint cluster region-related), BAIAP3 (BAI1-associated protein 3), BCR (breakpoint cluster region), C2CD2 (C2 calcium dependent domain containing 2), C2CD3 (C2 calcium dependent domain containing 3), CADPS (calcium-dependent secretion activator 1), CADPS2 (calcium-dependent secretion activator 2), CAPN5 (calpain-5), CAPN6 (calpain-6), CC2D1A (coiled-coil and C2 domain-containing protein 1A), CC2D1B (coiled-coil and C2 domain-containing protein 1B), CPNE1 (copine-1), CPNE2 (copine-2), CPNE3 (copine-3), CPNE4 (copine-4), CPNE5 (copine-5), CPNE6 (copine-6), CPNE7 (copine-7), CPNE8 (copine-8), CPNE9 (copine-9), DAB2IP (disabled homolog 2-interacting protein), DOC2A (double C2-like domain-containing protein alpha), DOC2B (double C2-like domain-containing protein beta), DYSF (dysferlin), ESYT1 (extended synaptotagmin-1), ESYT3 (extended synaptotagmin-3), FAM62B (extended synaptotagmin-2), FER1L3 (myoferlin), FER1L5 (fer-1 like family member 5), HECW1 (C2 and WW domain containing E3 ubiquitin protein ligase 1), HECW2 (C2 and WW domain containing E3 ubiquitin protein ligase 1), ITCH (itchy E3 ubiquitin protein ligase), ITSN1 (intersectin-1), ITSN2 (intersectin-2), MCTP1 (multiple C2 and transmembrane domain containing 1), MCTP2 (multiple C2 and transmembrane domain containing 2), MTAC2D1 (tandem C2 domains nuclear protein), NEDD4 (neural precursor cell expressed developmentally down-regulated protein 4), NEDD4L (neural precursor cell expressed developmentally down-regulated gene 4-like), OTOF (otoferlin), PCLO (protein piccolo), PIK3C2A (phosphatidylinositol-4-phosphate 3-kinase C2 domain-containing alpha), PIK3C2B (phosphatidylinositol-4-phosphate 3-kinase C2 domain-containing beta), PIK3C2G (phosphatidylinositol-4-phosphate 3-kinase C2 domain-containing gamma), PLA2G4A (cytosolic phospholipase A2), PLA2G4B (cytosolic phospholipase A2 beta), PLA2G4D (cytosolic phospholipase A2 delta), PLA2G4E (cytosolic phospholipase A2 epsilon), PLA2G4F (cytosolic phospholipase A2 zeta), PLCB 1 (1-phosphatidylinositol-4,5-bisphosphate phosphodiesterase beta-1), PLCB 2 (1-phosphatidylinositol-4,5-bisphosphate phosphodiesterase beta-2), PLCB 3 (1-phosphatidylinositol-4,5-bisphosphate phosphodiesterase beta-3), PLCB 4 (1-phosphatidylinositol-4,5-bisphosphate phosphodiesterase beta-4), PLCD1 (phospholipase C delta 1), PLCD3 (phospholipase C delta 3), PLCD4 (phospholipase C delta 4), PLCE1 (phospholipase C epsilon 1), PLCG1 (phospholipase C gamma 1), PLCG2 (phospholipase C gamma 2), PLCH1 (phospholipase C eta 1), PLCH2 (phospholipase C eta 2), PLCL1 (phospholipase C like 1), PLCL2 (phospholipase C like 2), PLCZ1 (phospholipase C zeta 1), PRF1 (perforin-1), PRKCA (protein kinase C alpha), PRKCB1(protein kinase C beta type), PRKCE(protein kinase C epsilon), PRKCG (protein kinase C gamma), PRKCH (protein kinase C eta), RAB11FIP1 (Rab11 family-interacting protein 1), RAB11FIP2 (Rab11 family-interacting protein 2), RAB11FIP5 (Rab11 family-interacting protein 5), RASA1 (RAS p21 protein activator 1), RASA2 (RAS p21 protein activator 2), RASA3 (RAS p21 protein activator 3), RASA4 (RAS p21 protein activator 4), RASAL1 (RAS protein activator like 1), RASAL2 (RAS protein activator like 2), RGS3 (regulator of G-protein signaling 3), RIMS1 (regulating synaptic membrane exocytosis protein 1), RIMS2 (regulating synaptic membrane exocytosis protein 2), RIMS3 (regulating synaptic membrane exocytosis protein 3), RIMS4 (regulating synaptic membrane exocytosis protein 4), RPGRIP1 (X-linked retinitis pigmentosa GTPase regulator-interacting protein 1), RPH3A (rabphilin-3A), SMURF1 (E3 ubiquitin-protein ligase SMURF1), SMURF2 (E3 ubiquitin-protein ligase SMURF2), SYNGAP1 (synaptic Ras GTPase-activating protein 1), SYT1 (synaptotagmin-1), SYT10 (synaptotagmin-10), SYT11 (synaptotagmin-11), SYT12 (synaptotagmin-12), SYT13 (synaptotagmin-13), SYT14 (synaptotagmin-14), SYT15 (synaptotagmin-15), SYT16 (synaptotagmin-16), SYT17 (synaptotagmin-17), SYT2 (synaptotagmin-2), SYT3 (synaptotagmin-3), SYT4 (synaptotagmin-4), SYT5 (synaptotagmin-5), SYT6 (synaptotagmin-6), SYT7 (synaptotagmin-7), SYT8 (synaptotagmin-8), SYT9 (synaptotagmin-9), SYTL1 (synaptotagmin like 1), SYTL2 (synaptotagmin like 2), SYTL3 (synaptotagmin like 3), SYTL4 (synaptotagmin like 4), SYTL5 (synaptotagmin like 5), TOLLIP (toll interacting protein), UNC13A (Unc-13 homolog A), UNC13B (Unc-13 homolog B), UNC13C (Unc-13 homolog C), UNC13D (Unc-13 homolog D), WWC2 (WW and C2 domain containing 2), WWP1 (WW domain containing E3 ubiquitin protein ligase 1), WWP2 (WW domain containing E3 ubiquitin protein ligase 2), and PTEN (phosphatase and tensin homolog).

\* \* \* \* \*

SEQUENCE LISTING

<160> NUMBER OF SEQ ID NOS: 17

<210> SEQ ID NO 1

```
<211> LENGTH: 35
<212> TYPE: DNA
<213> ORGANISM: Artificial
<220> FEATURE:
<223> OTHER INFORMATION: hPKC beta1_C2_PN127(NcoI)

<400> SEQUENCE: 1
aaaccatggg ccaccagggg atgaaatgtg acacc                         35

<210> SEQ ID NO 2
<211> LENGTH: 63
<212> TYPE: DNA
<213> ORGANISM: Artificial
<220> FEATURE:
<223> OTHER INFORMATION: hPKC beta1_C2_PC296(XhoI)

<400> SEQUENCE: 2
aaactcgagc agatcctctt ctgagatgag tttttgttcc tcacttcctt ctggtggcac    60
agg                                                                  63

<210> SEQ ID NO 3
<211> LENGTH: 29
<212> TYPE: DNA
<213> ORGANISM: Artificial
<220> FEATURE:
<223> OTHER INFORMATION: hAkt1_PH_PN1(SacI)

<400> SEQUENCE: 3
aaagagctca tgggcagcga cgtggctat                                29

<210> SEQ ID NO 4
<211> LENGTH: 50
<212> TYPE: DNA
<213> ORGANISM: Artificial
<220> FEATURE:
<223> OTHER INFORMATION: hAKT1_PH_PC144(SpeI)

<400> SEQUENCE: 4
aaaactagtt cagtggtggt ggtggtggtg gcggtgcttg ggcttggcca         50

<210> SEQ ID NO 5
<211> LENGTH: 32
<212> TYPE: DNA
<213> ORGANISM: Artificial
<220> FEATURE:
<223> OTHER INFORMATION: hPKC beta1_C2_PN159(BglII)

<400> SEQUENCE: 5
aaaagatcta tgcgcggccg catctacatc ca                            32

<210> SEQ ID NO 6
<211> LENGTH: 29
<212> TYPE: DNA
<213> ORGANISM: Artificial
<220> FEATURE:
<223> OTHER INFORMATION: hPKC beta1_C2_PC289(BanHI)

<400> SEQUENCE: 6
aaaggatcca ggcacattga agtactcgc                                29

<210> SEQ ID NO 7
<211> LENGTH: 30
<212> TYPE: DNA
<213> ORGANISM: Artificial
<220> FEATURE:
<223> OTHER INFORMATION: hAkt1_PH_PN6(BglII)
```

<400> SEQUENCE: 7
aaaagatcta tgattgtgaa ggagggttgg                                               30

<210> SEQ ID NO 8
<211> LENGTH: 27
<212> TYPE: DNA
<213> ORGANISM: Artificial
<220> FEATURE:
<223> OTHER INFORMATION: hAkt1_PH_PN111(BamHI)

<400> SEQUENCE: 8
aaaggatccc ttgaggccgt cagccac                                                  27

<210> SEQ ID NO 9
<211> LENGTH: 31
<212> TYPE: DNA
<213> ORGANISM: Artificial
<220> FEATURE:
<223> OTHER INFORMATION: hPKC beta1_C2_PN127(BglII)

<400> SEQUENCE: 9
aaaagatctc gctcattgtc ctcgtaagag a                                             31

<210> SEQ ID NO 10
<211> LENGTH: 29
<212> TYPE: DNA
<213> ORGANISM: Artificial
<220> FEATURE:
<223> OTHER INFORMATION: hPKC beta1_C2_PC296(NheI)

<400> SEQUENCE: 10
aaagctagcg gacaaagatc ccatgaagt                                                29

<210> SEQ ID NO 11
<211> LENGTH: 29
<212> TYPE: DNA
<213> ORGANISM: Artificial
<220> FEATURE:
<223> OTHER INFORMATION: hAKT1_kinase_PN(NheI)

<400> SEQUENCE: 11
aaagctagct ttgagtacct gaagctgct                                                29

<210> SEQ ID NO 12
<211> LENGTH: 29
<212> TYPE: DNA
<213> ORGANISM: Artificial
<220> FEATURE:
<223> OTHER INFORMATION: hAKT1_kinase_PC(KpnI)

<400> SEQUENCE: 12
aaaggtacct caggccgtgc cgctggccg                                                29

<210> SEQ ID NO 13
<211> LENGTH: 144
<212> TYPE: PRT
<213> ORGANISM: Artificial
<220> FEATURE:
<223> OTHER INFORMATION: PH domain of Akt protein

<400> SEQUENCE: 13

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp

```
                    20                  25                  30

Gly Thr Phe Ile Gly Tyr Lys Glu Arg Pro Gln Asp Val Asp Gln Arg
                35                  40                  45

Glu Ala Pro Leu Asn Asn Phe Ser Val Ala Gln Cys Gln Leu Met Lys
         50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
                100                 105                 110

Gln Glu Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

<210> SEQ ID NO 14
<211> LENGTH: 124
<212> TYPE: PRT
<213> ORGANISM: Artificial
<220> FEATURE:
<223> OTHER INFORMATION: C2 domain of PKC beta protein

<400> SEQUENCE: 14

His Gln Gly Met Lys Cys Asp Thr Cys Met Met Asn Val His Lys Arg
 1               5                  10                  15

Cys Val Met Asn Val Pro Ser Leu Cys Gly Thr Asp His Thr Glu Arg
                20                  25                  30

Arg Gly Arg Ile Tyr Ile Gln Ala His Ile Asp Arg Asp Val Leu Ile
            35                  40                  45

Val Leu Val Arg Asp Ala Lys Asn Leu Val Pro Met Asp Pro Asn Gly
        50                  55                  60

Leu Ser Asp Pro Tyr Val Lys Leu Lys Leu Ile Pro Asp Pro Lys Ser
 65                  70                  75                  80

Glu Ser Lys Gln Lys Thr Lys Thr Ile Lys Cys Ser Leu Asn Pro Glu
                85                  90                  95

Trp Asn Glu Thr Phe Arg Phe Gln Leu Lys Glu Ser Asp Lys Asp Arg
            100                 105                 110

Arg Leu Ser Val Glu Ile Trp Asp Trp Asp Leu Thr
        115                 120

<210> SEQ ID NO 15
<211> LENGTH: 370
<212> TYPE: PRT
<213> ORGANISM: Artificial
<220> FEATURE:
<223> OTHER INFORMATION: Akt protein w/o PH domain

<400> SEQUENCE: 15

Lys Lys Gln Glu Glu Glu Met Asp Phe Arg Ser Gly Ser Pro Ser
 1               5                  10                  15

Asp Asn Ser Gly Ala Glu Glu Met Glu Val Ser Leu Ala Lys Pro Lys
                20                  25                  30

His Arg Val Thr Met Asn Glu Phe Glu Tyr Leu Lys Leu Leu Gly Lys
            35                  40                  45

Gly Thr Phe Gly Lys Val Ile Leu Val Lys Glu Lys Ala Thr Gly Arg
        50                  55                  60
```

Tyr Tyr Ala Met Lys Ile Leu Lys Lys Glu Val Ile Val Ala Lys Asp
65                  70                  75                  80

Glu Val Ala His Thr Leu Thr Glu Asn Arg Val Leu Gln Asn Ser Arg
                85                  90                  95

His Pro Phe Leu Thr Ala Leu Lys Tyr Ser Phe Gln Thr His Asp Arg
            100                 105                 110

Leu Cys Phe Val Met Glu Tyr Ala Asn Gly Gly Leu Phe Phe His
        115                 120                 125

Leu Ser Arg Glu Arg Val Phe Ser Glu Asp Arg Ala Arg Phe Tyr Gly
    130                 135                 140

Ala Glu Ile Val Ser Ala Leu Asp Tyr Leu His Ser Glu Lys Asn Val
145                 150                 155                 160

Val Tyr Arg Asp Leu Lys Leu Glu Asn Leu Met Leu Asp Lys Asp Gly
                165                 170                 175

His Ile Lys Ile Thr Asp Phe Gly Leu Cys Lys Glu Gly Ile Lys Asp
            180                 185                 190

Gly Ala Thr Met Lys Thr Phe Cys Gly Thr Pro Glu Tyr Leu Ala Pro
        195                 200                 205

Glu Val Leu Glu Asp Asn Asp Tyr Gly Arg Ala Val Asp Trp Trp Gly
    210                 215                 220

Leu Gly Val Val Met Tyr Glu Met Met Cys Gly Arg Leu Pro Phe Tyr
225                 230                 235                 240

Asn Gln Asp His Glu Lys Leu Phe Glu Leu Ile Leu Met Glu Glu Ile
                245                 250                 255

Arg Phe Pro Arg Thr Leu Gly Pro Glu Ala Lys Ser Leu Leu Ser Gly
            260                 265                 270

Leu Leu Lys Lys Asp Pro Lys Gln Arg Leu Gly Gly Gly Ser Glu Asp
        275                 280                 285

Ala Lys Glu Ile Met Gln His Arg Phe Phe Ala Gly Ile Val Trp Gln
    290                 295                 300

His Val Tyr Glu Lys Lys Leu Ser Pro Pro Phe Lys Pro Gln Val Thr
305                 310                 315                 320

Ser Glu Thr Asp Thr Arg Tyr Phe Asp Glu Glu Phe Thr Ala Gln Met
                325                 330                 335

Ile Thr Ile Thr Pro Pro Asp Gln Asp Asp Ser Met Glu Cys Val Asp
            340                 345                 350

Ser Glu Arg Arg Pro His Phe Pro Gln Phe Ser Tyr Ser Ala Ser Gly
        355                 360                 365

Thr Ala
370

<210> SEQ ID NO 16
<211> LENGTH: 480
<212> TYPE: PRT
<213> ORGANISM: Artificial
<220> FEATURE:
<223> OTHER INFORMATION: Akt protein

<400> SEQUENCE: 16

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
                20                  25                  30

Gly Thr Phe Ile Gly Tyr Lys Glu Arg Pro Gln Asp Val Asp Gln Arg
            35                  40                  45

```
Glu Ala Pro Leu Asn Asn Phe Ser Val Ala Gln Cys Gln Leu Met Lys
    50                  55                  60
Thr Glu Arg Pro Arg Pro Asn Thr Phe Ile Ile Arg Cys Leu Gln Trp
65                  70                  75                  80
Thr Thr Val Ile Glu Arg Thr Phe His Val Glu Thr Pro Glu Arg
                85                  90                  95
Glu Glu Trp Thr Thr Ala Ile Gln Thr Val Ala Asp Gly Leu Lys Lys
            100                 105                 110
Gln Glu Glu Glu Met Asp Phe Arg Ser Gly Ser Pro Ser Asp Asn
            115                 120                 125
Ser Gly Ala Glu Glu Met Glu Val Ser Leu Ala Lys Pro Lys His Arg
130                 135                 140
Val Thr Met Asn Glu Phe Glu Tyr Leu Lys Leu Leu Gly Lys Gly Thr
145                 150                 155                 160
Phe Gly Lys Val Ile Leu Val Lys Glu Lys Ala Thr Gly Arg Tyr Tyr
                165                 170                 175
Ala Met Lys Ile Leu Lys Lys Glu Val Ile Val Ala Lys Asp Glu Val
            180                 185                 190
Ala His Thr Leu Thr Glu Asn Arg Val Leu Gln Asn Ser Arg His Pro
        195                 200                 205
Phe Leu Thr Ala Leu Lys Tyr Ser Phe Gln Thr His Asp Arg Leu Cys
    210                 215                 220
Phe Val Met Glu Tyr Ala Asn Gly Gly Glu Leu Phe Phe His Leu Ser
225                 230                 235                 240
Arg Glu Arg Val Phe Ser Glu Asp Arg Ala Arg Phe Tyr Gly Ala Glu
                245                 250                 255
Ile Val Ser Ala Leu Asp Tyr Leu His Ser Glu Lys Asn Val Val Tyr
            260                 265                 270
Arg Asp Leu Lys Leu Glu Asn Leu Met Leu Asp Lys Asp Gly His Ile
        275                 280                 285
Lys Ile Thr Asp Phe Gly Leu Cys Lys Glu Gly Ile Lys Asp Gly Ala
    290                 295                 300
Thr Met Lys Thr Phe Cys Gly Thr Pro Glu Tyr Leu Ala Pro Glu Val
305                 310                 315                 320
Leu Glu Asp Asn Asp Tyr Gly Arg Ala Val Asp Trp Trp Gly Leu Gly
                325                 330                 335
Val Val Met Tyr Glu Met Met Cys Gly Arg Leu Pro Phe Tyr Asn Gln
            340                 345                 350
Asp His Glu Lys Leu Phe Glu Leu Ile Leu Met Glu Glu Ile Arg Phe
        355                 360                 365
Pro Arg Thr Leu Gly Pro Glu Ala Lys Ser Leu Leu Ser Gly Leu Leu
    370                 375                 380
Lys Lys Asp Pro Lys Gln Arg Leu Gly Gly Gly Ser Glu Asp Ala Lys
385                 390                 395                 400
Glu Ile Met Gln His Arg Phe Phe Ala Gly Ile Val Trp Gln His Val
                405                 410                 415
Tyr Glu Lys Lys Leu Ser Pro Pro Phe Lys Pro Gln Val Thr Ser Glu
            420                 425                 430
Thr Asp Thr Arg Tyr Phe Asp Glu Phe Thr Ala Gln Met Ile Thr
        435                 440                 445
Ile Thr Pro Pro Asp Gln Asp Asp Ser Met Glu Cys Val Asp Ser Glu
    450                 455                 460
Arg Arg Pro His Phe Pro Gln Phe Ser Tyr Ser Ala Ser Gly Thr Ala
```

<210> SEQ ID NO 17
<211> LENGTH: 667
<212> TYPE: PRT
<213> ORGANISM: Artificial
<220> FEATURE:
<223> OTHER INFORMATION: C2-Akt fusion protein

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Arg Thr Gln Ile Ser Leu Ile Val Leu Arg Asp Ala Lys Asn
                245                 250                 255

Leu Val Pro Met Asp Pro Asn Gly Leu Ser Asp Pro Tyr Val Lys Leu
            260                 265                 270

Lys Leu Ile Pro Asp Pro Lys Ser Glu Ser Lys Gln Lys Thr Lys Thr
        275                 280                 285

Ile Lys Cys Ser Leu Asn Pro Glu Trp Asn Glu Thr Phe Arg Phe Gln
290                 295                 300

Leu Lys Glu Ser Asp Lys Asp Arg Arg Leu Ser Val Glu Ile Trp Asp
305                 310                 315                 320

Trp Asp Leu Thr Ser Arg Asn Asp Phe Met Gly Ser Leu Ser Ala Ser
                325                 330                 335

Phe Glu Tyr Leu Lys Leu Leu Gly Lys Gly Thr Phe Gly Lys Val Ile
            340                 345                 350

Leu Val Lys Glu Lys Ala Thr Gly Arg Tyr Tyr Ala Met Lys Ile Leu

```
              355                 360                 365
Lys Lys Glu Val Ile Val Ala Lys Asp Glu Val Ala His Thr Leu Thr
        370                 375                 380

Glu Asn Arg Val Leu Gln Asn Ser Arg His Pro Phe Leu Thr Ala Leu
385                 390                 395                 400

Lys Tyr Ser Phe Gln Thr His Asp Arg Leu Cys Phe Val Met Glu Tyr
                405                 410                 415

Ala Asn Gly Gly Glu Leu Phe Phe His Leu Ser Arg Glu Arg Val Phe
            420                 425                 430

Ser Glu Asp Arg Ala Arg Phe Tyr Gly Ala Glu Ile Val Ser Ala Leu
        435                 440                 445

Asp Tyr Leu His Ser Glu Lys Asn Val Val Tyr Arg Asp Leu Lys Leu
    450                 455                 460

Glu Asn Leu Met Leu Asp Lys Asp Gly His Ile Lys Ile Thr Asp Phe
465                 470                 475                 480

Gly Leu Cys Lys Glu Gly Ile Lys Asp Gly Ala Thr Met Lys Thr Phe
                485                 490                 495

Cys Gly Thr Pro Glu Tyr Leu Ala Pro Glu Val Leu Glu Asp Asn Asp
            500                 505                 510

Tyr Gly Arg Ala Val Asp Trp Trp Gly Leu Gly Val Val Met Tyr Glu
        515                 520                 525

Met Met Cys Gly Arg Leu Pro Phe Tyr Asn Gln Asp His Glu Lys Leu
    530                 535                 540

Phe Glu Leu Ile Leu Met Glu Glu Ile Arg Phe Pro Arg Thr Leu Gly
545                 550                 555                 560

Pro Glu Ala Lys Ser Leu Leu Ser Gly Leu Leu Lys Lys Asp Pro Lys
                565                 570                 575

Gln Arg Leu Gly Gly Gly Ser Glu Asp Ala Lys Glu Ile Met Gln His
            580                 585                 590

Arg Phe Phe Ala Gly Ile Val Trp Gln His Val Tyr Glu Lys Lys Leu
        595                 600                 605

Ser Pro Pro Phe Lys Pro Gln Val Thr Ser Glu Thr Asp Thr Arg Tyr
    610                 615                 620

Phe Asp Glu Glu Phe Thr Ala Gln Met Ile Thr Ile Thr Pro Pro Asp
625                 630                 635                 640

Gln Asp Asp Ser Met Glu Cys Val Asp Ser Glu Arg Arg Pro His Phe
                645                 650                 655

Pro Gln Phe Ser Tyr Ser Ala Ser Gly Thr Ala
            660                 665
```